(12) United States Patent
Wright et al.

(10) Patent No.: US 12,198,570 B2
(45) Date of Patent: Jan. 14, 2025

(54) DETERMINATION OF SURGICAL PERFORMANCE LEVEL

(71) Applicant: Sony Group Corporation, Tokyo (JP)

(72) Inventors: Christopher Wright, London (GB); Nicholas Walker, London (GB); Akinori Kamoda, Tokyo (JP)

(73) Assignee: Sony Group Corporation, Tokyo (JP)

( * ) Notice: Subject to any disclaimer, the term of this patent is extended or adjusted under 35 U.S.C. 154(b) by 0 days.

(21) Appl. No.: 18/010,217

(22) PCT Filed: Jun. 18, 2021

(86) PCT No.: PCT/JP2021/023147
§ 371 (c)(1),
(2) Date: Dec. 14, 2022

(87) PCT Pub. No.: WO2022/014255
PCT Pub. Date: Jan. 20, 2022

(65) Prior Publication Data
US 2023/0298482 A1 Sep. 21, 2023

(30) Foreign Application Priority Data

Jul. 14, 2020 (EP) .................................... 20185757

(51) Int. Cl.
*G09B 19/24* (2006.01)
*G16H 40/20* (2018.01)
*G16H 70/20* (2018.01)

(52) U.S. Cl.
CPC ............. *G09B 19/24* (2013.01); *G16H 40/20* (2018.01); *G16H 70/20* (2018.01)

(58) Field of Classification Search
CPC ........ G09B 19/24; G16H 40/20; G16H 70/20; G16H 80/00; A61B 1/00183; A61B 2034/2055
See application file for complete search history.

(56) References Cited

U.S. PATENT DOCUMENTS

| | | | | |
|---|---|---|---|---|
| 2009/0043801 A1* | 2/2009 | LeClair | ................... | G16Z 99/00 707/999.102 |
| 2009/0259488 A1* | 10/2009 | Gounares | ............... | G16H 70/20 705/7.42 |
| 2013/0093829 A1* | 4/2013 | Rosenblatt | ............... | H04N 7/18 434/365 |

(Continued)

FOREIGN PATENT DOCUMENTS

WO 2018/217407 A1 11/2018

OTHER PUBLICATIONS

International Search Report and Written Opinion mailed on Sep. 29, 2021, received for PCT Application PCT/JP2021/023147, filed on Jun. 18, 2021, 9 pages including English Translation.

*Primary Examiner* — Peter R Egloff
(74) *Attorney, Agent, or Firm* — XSENSUS LLP

(57) ABSTRACT

A surgical training system comprising circuitry configured to: obtain surgical information recorded during each of a plurality of surgical performances occurring at a plurality of identified times by each of a plurality of surgeons in a surgeon network; determine a level of influence of each surgeon using the surgical information and the identified times; and output an identifier of a surgeon with a level of influence which meets a predetermined condition as a candidate for receiving training.

19 Claims, 16 Drawing Sheets

(56) References Cited

U.S. PATENT DOCUMENTS

| | | | |
|---|---|---|---|
| 2014/0127660 A1* | 5/2014 | Rappel | G09B 23/30 |
| | | | 434/262 |
| 2014/0163736 A1* | 6/2014 | Azizian | A61B 34/20 |
| | | | 700/259 |
| 2014/0276855 A1* | 9/2014 | de la Barrera | A61B 17/154 |
| | | | 705/2 |
| 2017/0116873 A1* | 4/2017 | Lendvay | G09B 5/02 |
| 2018/0247128 A1 | 8/2018 | Alvi et al. | |
| 2018/0330232 A1* | 11/2018 | Ronayne | G09B 5/00 |
| 2019/0000569 A1* | 1/2019 | Crawford | A61B 34/20 |

* cited by examiner

| Characteristic | Surgeon A | Surgeon B | Surgeon C |
|---|---|---|---|
| First incision blood vessel | 100R | 100R | 100L |
| Scalpel angle | 20° | 45° | 25° |
| Scalpel speed | 2.5cms$^{-1}$ | 3.0cms$^{-1}$ | 3.2cms$^{-1}$ |
| Outcome score | +0.5 | +0.75 | -0.25 |

FIG. 3

| Factor | -1 | -0.5 | 0 | +0.5 | +1.0 | Weighting |
|---|---|---|---|---|---|---|
| Survival | Died | N/A | N/A | N/A | Survived | N/A |
| Complications | More than expected and at least one severe | More than expected or at least one severe | Number as expected, none severe | Fewer than expected, none severe | None | 1.5 |
| Unintended consequences | More than expected and at least one permanent | More than expected or at least one permanent | Number as expected, none permanent | Fewer than expected, none permanent | None | 1.5 |
| Recovery time | > 2 months more | 1-2 months more | As expected | 1-2 months less | > 2 months less | 0.5 |
| Scarring | Permanently worse than expected | Worse than expected, not permanent | As expected | Less visible | Not visible | 0.25 |
| Blood Loss | >7% | ≤7% | ≤5% | ≤3% | ≤1% | 1.25 |

FIG. 4

DETERMINATION OF SURGICAL PERFORMANCE LEVEL

CROSS-REFERENCE TO RELATED APPLICATIONS

The present application is based on PCT filing PCT/JP2021/023147, filed Jun. 18, 2021, which claims priority to EP 20185757.0, filed Jul. 14, 2020, the entire contents of each are incorporated herein by reference.

TECHNICAL FIELD

The present disclosure relates to a surgical training system and method.

BACKGROUND

The "background" description provided is for the purpose of generally presenting the context of the disclosure. Work of the presently named inventors, to the extent it is described in the background section, as well as aspects of the description which may not otherwise qualify as prior art at the time of filing, are neither expressly or impliedly admitted as prior art against the present disclosure.

Modern data capture and analysis methods allow characteristics of a surgical procedure (e.g. the way surgical instruments are held or the order in which tasks are completed) to be determined using information gathered from, for example, video footage or instrument data collected during the surgical procedure. This allows the characteristics associated with different surgeons (e.g. those with different skill levels, such as medical students and consultants) to be recognised.

There is a desire to do more with this information, however. In particular, it is desirable to use surgical characteristic information to determine the skills surgeons need to be trained with and the surgeons who it is most beneficial to train.

SUMMARY

The present disclosure is defined by the claims.

BRIEF DESCRIPTION OF DRAWINGS

Non-limiting embodiments and advantages of the present disclosure will be best understood by reference to the following detailed description taken in conjunction with the accompanying drawings.

FIG. 3 shows a table of recorded surgical characteristics.

FIG. 4 shows a table of measurement values and weightings used for determining an outcome score.

Like reference numerals designate identical or corresponding parts throughout the drawings.

DESCRIPTION OF EMBODIMENTS

Figure 1:
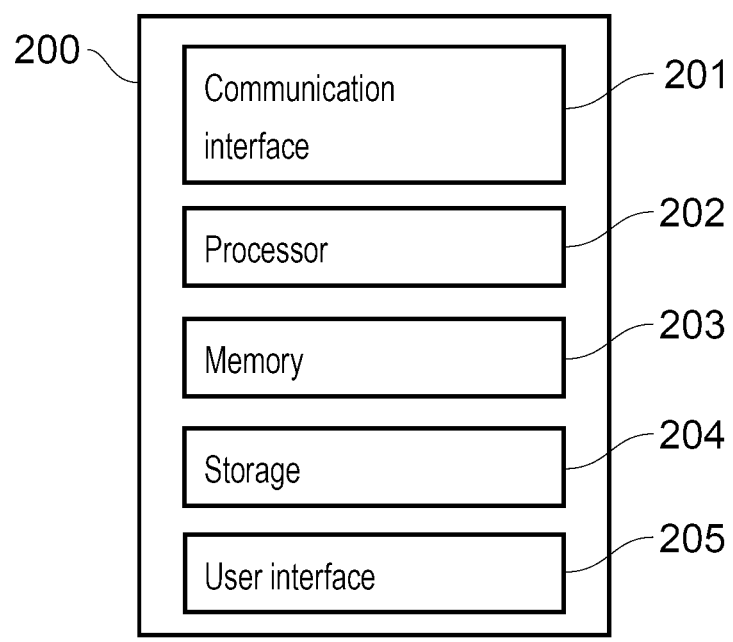
FIG. 1 shows a surgical training system according to an embodiment.

FIG. 1 shows a surgical training system (apparatus) 200 according to an embodiment. It comprises a communication interface 201 for sending electronic information to and/or receiving electronic information from one or more electronic devices (e.g. a digital surgical still image or moving image camera, a data-gathering information processing device comprised in a surgical instrument or an electronic display), a processor 202 for processing electronic instructions, a memory 203 for storing the electronic instructions to be processed and input and output data associated with the electronic instructions, a storage medium 204 (e.g. a hard disk drive, solid state drive or tape drive) for long term storage of data and a user interface 205 (e.g. a touch screen, a non-touch screen, buttons, a keyboard and/or a mouse) for receiving commands from and/or outputting information to a user. Each of the communication interface 201, processor 202, memory 203, storage medium 204 and user interface 205 are implemented using appropriate circuitry, for example. The processor 202 controls the operation of each of the communication interface 201, memory 203, storage medium 204 and user interface 205.

Figure 2:
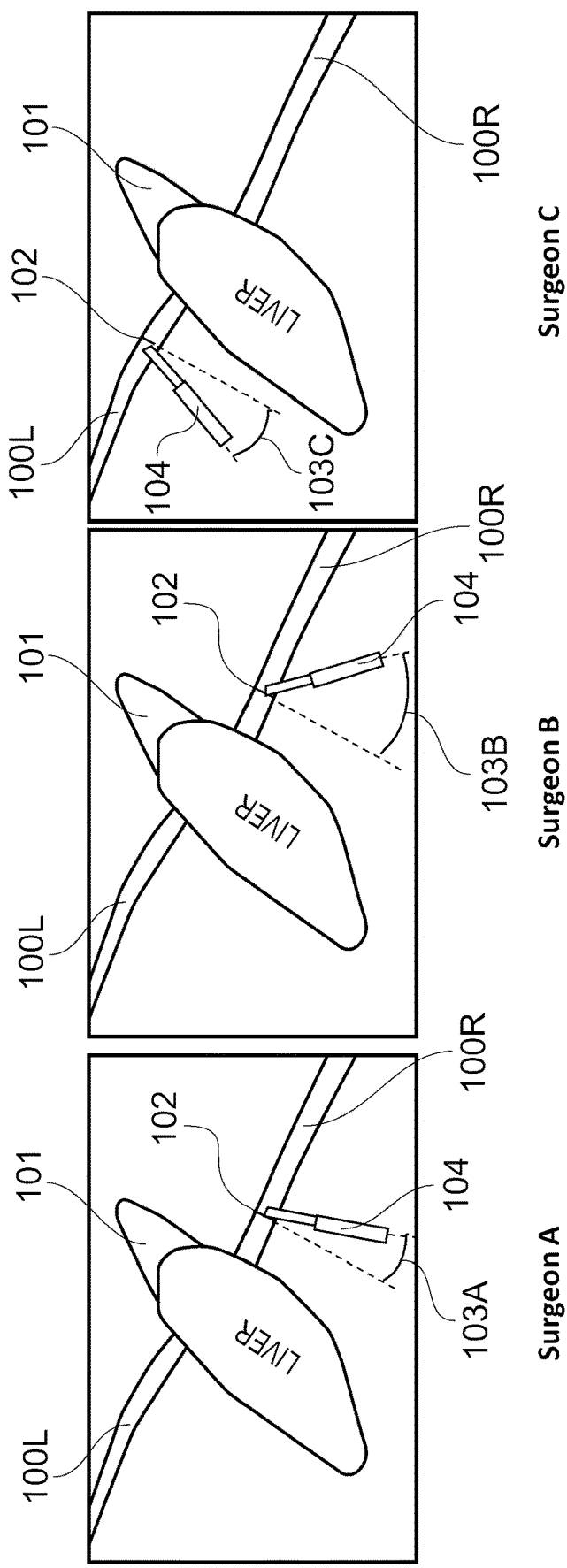
FIG. 2 shows part of the same type of surgical procedure being carried out by different surgeons.

FIG. 2 shows part of the same type of surgical procedure being carried out by different surgeons A, B and C. In this example, the surgical procedure is a liver transplant. The part of the surgical procedure is a first incision of a blood vessel attached to the liver 101. Several characteristics of the surgery (surgical characteristics) are different for different surgeons. These are which blood vessel is subject to the first incision (the first incision blood vessel), the angle of the scalpel 104 relative to the horizontal when making the first incision (the view of the surgery in FIG. 2 is as seen by the surgeon carrying out the surgery) and the speed of the scalpel as the incision is made. For ease of explanation, only three characteristics are considered. However, in reality, a much larger number of characteristics may be considered. Other characteristics could include surgical strategy decisions (e.g. the route taken by a surgeon along a surgical decision tree comprising decisions such as surgical techniques to use, incision locations, tools to use and contingency plans for various expected complications—see US patent application US 20180247128, for example), surgical tool selection, surgical tool settings or the surgical tool manipulation type, grip position and/or force used by the surgeon, for example. The characteristics are summarised in the table of FIG. 3 and are recorded in the storage medium 204.

Regarding the first incision blood vessel, there are two blood vessels which may be chosen, vessel 100L and vessel 100R (in reality, there may be a larger number of first incision blood vessels from which to choose). Surgeons A and B choose vessel 100R as the first incision blood vessel. Surgeon C, on the other hand, chooses vessel 100L as the first incision blood vessel. The selected first incision blood vessel is detected by the processor 202 for each surgeon using images of the surgery captured by a surgical camera such as an endoscope or a microscope (not shown) and transmitted to the communication interface 201. An object recognition technique is used to detect each blood vessel 100L and 100R in the image and to detect the first incision 102 made by the scalpel 104, thereby determining the first incision blood vessel. Any suitable objection recognition technique known in the art (e.g. a machine learning algorithm trained using previous images of blood vessels and incisions) may be used. The field of view of the surgical site of the images captured for each surgeon is the same to allow the first incision blood vessel of each surgeon to be identified based on its position in the image relative to the other detected blood vessels. This is demonstrated in FIG. 2 in which vessel 100L appears on the left and vessel 100R appears on the right for each of surgeons A, B and C.

Regarding the scalpel angle, the scalpel angle 103A of surgeon A is recorded as 20°, the scalpel angle 103B of surgeon B is recorded as 45° and the scalpel angle 103C of surgeon C is recorded as 25°.

The scalpel angle is determined by the processor 202 for each surgeon again using images of the surgery. An object recognition technique is used to detect the scalpel 104 (e.g. using a machine learning algorithm trained using previous images of scalpels) and the angle of the scalpel may be determined using a predetermined mapping between scalpel orientation in the image and scalpel angle with the horizontal. The predetermined mapping is stored in the storage medium 204. In an embodiment, a mapping between the 2D captured images of the surgical scene and a 3D model of the surgical scene is determined in advance and stored in the storage medium 204 to allow the scalpel angle to be determined from its orientation in the 2D captured images. 2D captured images of a single surgical scene may be simultaneously captured from a plurality of different fields of view (using a plurality of respective cameras) to improve the accuracy of the 2D to 3D mapping and therefore the accuracy of the determined scalpel angle.

Alternatively or in addition, the scalpel may comprise a gyro sensor or the like (not shown) which determines the orientation of the scalpel relative to gravity determined direction. Data output by the gyro sensor (this data being an example of surgical tool data) is transmitted to the communication interface 201. A predetermined mapping between the gyro sensor data and the scalpel angle with the horizontal is stored in the storage medium 204 and used by the processor 202 to determine the scalpel angle.

Regarding the scalpel speed when making the incision 102, surgeon A has a scalpel speed of 2.5 cms$^{-1}$ (centimetres per second), surgeon B has a scalpel speed of 3.0 cms$^{-1}$ and surgeon C has a scalpel speed of 3.2 cms$^{-1}$.

The scalpel speed is determined by the processor 202 for each surgeon again using images of the surgery. The change in position of the end of the scalpel 104 which intersects with the incision 102 (both the scalpel and incision previously having been detected as objects in the image) is tracked in successively captured images. The change in position is used together with (i) a predetermined mapping of image pixel pitch to distance in the surgical scene and (ii) the frame rate of the successively captured images to determine the speed at which the end of the scalpel is moving (and hence the speed at which the incision is being made). For example, if the distance between adjacent pixels in the captured images is determined to correspond to 0.005 cm in distance in the actual scene, the frame rate is 100 frames per second (fps) and a predetermined point on the end of the scalpel travels 5 pixels between successive frames, the scalpel speed is determined to be:

$$\frac{5[\text{pixels}] \times 0.005[\text{cm}]}{1/100\,[\text{fps}]} = 2.5[\text{cms}^{-1}] \qquad [\text{Math. 1}]$$

The predetermined pixel pitch to distance mapping and frame rate is stored in the storage medium 204.

Alternatively or in addition, the scalpel may comprise an accelerometer or the like (not shown) which determines the acceleration as the scalpel changes from being stationary (just before the surgeon starts the incision) to moving at a steady cutting speed (as the surgeon makes the incision). The acceleration (which is another example of surgical tool data) is multiplied by (or, for greater accuracy, numerically integrated over) the time period over which it occurs to determine the scalpel speed. In an embodiment, the accelerometer is a six axis accelerometer (measuring both linear and rotational acceleration along each of three perpendicular axes) and the processor 202 distinguishes acceleration of the scalpel when making the incision from acceleration caused by other types of movement (e.g. when the surgeon initially picks up the scalpel). For example, acceleration of the scalpel during making the incision is more likely to be linear along a relatively straight line with a low amount of rotational acceleration whereas acceleration when initially picking up the scalpel is more likely to include higher amounts of random rotational acceleration. In an embodiment, the processor 202 may use a machine learning algorithm trained using previous examples of six axis acceleration of a scalpel during incision and during other types of movement to detect acceleration caused by an incision. When the start of an incision is detected, the processor 202 beings timing the acceleration to determine the scalpel speed.

The surgical characteristics of FIG. 3 are collected from live surgery performed on a patient. However, more generally, surgical characteristics may also be determined through simulated surgery (e.g. using a surgical dummy or using a virtual reality training environment). Live and simulated surgeries are referred to more generally as surgical performances.

More generally, surgical characteristics may be determined from data collected by any suitable sensor or combination of sensors used in the surgery (e.g. on surgical instruments or a surgical robot used in the surgery). Such sensors may include optical sensors, time of flight sensors, accelerometers, pressure sensors, gyroscopes, infrared sensors, ultrasound probes or other relevant sensors. Optical sensors may include those found in smartphones, smart glasses, computers, operating room cameras, fluorescent microscopes or others. Surgical data generated from optical sensors could consist of RGB data or fluorescent imaging data (obtained by applying a fluorescent dye to the surgical site of the patient, for example) arranged in a 2D grid. Video processing algorithms can be used convert surgical data to 3D coordinate estimates. Fluorescence imaging may be used in combination with wavelengths of light outside of the visible spectrum. This may enable generation of surgical data from non-visible areas of the surgical site. Surgical data generated from time of flight sensors might be used to directly map the 3D surgical environment. Furthermore, Simultaneous Localisation And Mapping technology (SLAM) may be used to gather additional data of the 3D surgical environment. Example surgical instruments which may comprise such a sensor or set of sensors include scalpels, scissors, forceps, probes or cauterisers, for example.

The table of FIG. 3 also shows an outcome score for each surgeon. The outcome score indicates how successful the surgical procedure was for each of the surgeons. The outcome score is determined from one or more factors known to be indicative of the success of a surgical procedure. Example factors include whether or not the patient survives the surgery, the existence and severity of complications arising in the surgery (e.g. events that occurred which made the surgery more complicated and/or made it last longer), the existence and severity of unintended consequences of the surgery (e.g. a patient losing ability to do something they could do before the surgery), the patient's recovery period, the amount of scarring and the quantity of blood loss. After each surgery, the one or more factors are measured and the measurements are provided to the surgical training system via the user interface 205 (in the case of manual entry of the measurements) and/or communication interface 201 (in the case of automated measurements). A measurement may be manually input for factors such as the amount of scarring, for example. An automated measurement may be input for factors such as the quantity of blood loss (e.g. based on input from a machine (not shown) monitoring the patient's blood pressure which is able to estimate the amount of blood loss based on this). The measurements are then used to generate the outcome score. More generally, measurement values may be determined from electronic medical records, scans from medical nodes or voice recordings of a physician, for example.

The outcome score may take any appropriate format. In this example, the outcome score takes a value of between +1 and −1. An outcome score of +1 is the best possible outcome. An outcome score of −1 is the worse possible outcome. An outcome score of 0 indicates an average outcome. In an example, each individual factor contributing to the outcome score is assigned a measurement value of between +1 and −1. An average of the measurement values of each factor is then determined as the outcome score. Some factors may be deemed more important than others in affecting patient outcome. The calculated average may therefore be a waited average with greater weightings given to factors deemed the most important. In an example, the most important factor is whether the patient survives the surgery. If the patient does not service the surgery, the outcome score is always recorded as −1 (i.e. the worse possible outcome). On the other hand, if the patient survives, the outcome score is recorded as the average or weighted average of the remaining factors.

An example of how measurement values and weightings may be assigned for the factors mentioned above is shown in the table in FIG. 4. These may vary significantly for different types of surgery. The number and type of factors, how their measurement values are calculated (including the granularity of measurement values, e.g. a higher granularity so adjacent selectable measurement values are separated by, say, 0.25 instead of 0.5 is possible) and their weightings for different types of surgery may be determined in advance by experts in the medical community and stored in the storage medium 204.

As shown in the table of FIG. 4, a measurement value of −1 is given if the patient does not survive the surgery. In this case, the outcome score is set as −1. A measurement value of +1 is given if the patient does survive the surgery. In this case, the outcome score is determined as the weighted average of the remaining factors. The remaining factors can each take a measurement value of −1, −0.5, 0, +0.5 and +1.

The "complications" factor takes a value of 0 when the number of complications is as expected (e.g. within a threshold value equal to the average number of complications occurring for liver transplants in the medical community) and none of them are severe. A complication is classed as "severe" if one or more thresholds (e.g. the additional time added to the surgery because of the complication) are exceeded, for example. The "complications" factor takes a value of −0.5 if more complications occur than expected or if at least one of them is severe. It takes a value of −1 if both more complications occur than expected and at least one of them is severe. It takes a value of +0.5 if there are fewer complications than expected and none severe and a value of +1 if no complications occur.

The "unintended consequences" factor takes a value of 0 when the number of unintended consequences is as expected (e.g. within a threshold value equal to the average number of unintended consequences occurring for liver transplants in the medical community) and none of them are permanent. An unintended consequence is classed as "permanent" if it is expected to cause the patient's life to be permanently affected in a negative way (e.g. through chronic pain), for example. The "unintended consequences" factor takes a value of −0.5 if more unintended consequences occur than expected or if at least one of them is permanent. It takes a value of −1 if both more unintended consequences occur than expected and at least one of them is permanent. It takes a value of +0.5 if there are fewer unintended consequences than expected and none permanent and a value of +1 if no complications occur.

The "recovery time" factor takes a value of 0 when the recovery time is as expected (e.g. within a month of the average recovery time for liver transplants in the medical community). It takes a value of −0.5 if the recovery time is 1-2 months more than expected and a value of −1 if the recovery time is more than 2 months more than expected. It takes a value of +0.5 if the recovery time is 1-2 months less than expected and a value of +1 if the recovery time is more than 2 months less than expected.

The "scarring" factor takes a value of 0 when the amount of scarring is as expected. This is based, for example, on both initial scarring and how the scarring changes over time and is based on the opinion of the patient (e.g. who is contacted to give their opinion on the scarring at regular intervals after the surgery). The "scarring" factor takes a value of −0.5 if the scarring is worse than expected but not permanent (e.g. if the scarring is initially unacceptable to the patient but fades over time to an acceptable level). It takes a value of −1 if the scarring is worse than expected and permanent (e.g. if the scarring remains unacceptable to the patient even after a threshold amount of time, e.g. 1 year, has passed). It takes a value of +0.5 if the scarring is less visible than the patient expected and a value of +1 if the patient considers the scarring to not be visible at all.

The "blood loss" factor takes a value of 0 when the amount of blood loss is more than 3% but less than or equal to 5% of the patient's blood volume prior to the surgery. It takes a value of −0.5 if the amount of blood loss is more than 5% but less than or equal to 7%. It takes a value of −1 if the amount of blood loss is more than 7%. It takes a value of +0.5 if the amount of blood loss is more than 1% but less than or equal to 3%. It takes a value of +1 if the amount of blood loss is less than or equal to 1%. The amount of blood loss associated with each measurement value −1, −0.5, 0, +0.5 and 1 is determined based on the average amount of blood loss for liver transplants in the medical community, for example.

Thus, for each liver transplant, characteristics of the surgery (e.g. as in FIG. 3) and factors indicating the outcome of the surgery are recorded (e.g. as in FIG. 4). Over time, this allows surgical characteristics to be correlated with each other and with surgical outcomes. With enough data, it is possible to get an idea of the surgical characteristics which are more likely to produce favourable outcomes. These surgical characteristics can then be taught to surgeons to improve the outcome of surgeries in the future. For example, FIG. 3 indicates that the characteristics of blood vessel 100R being the first incision blood vessel, a scalpel angle of 45° and a scalpel speed of 3.0 $cms^{-1}$ results in the most favourable outcome score. If this finding is repeated over a statistically significant number of further liver transplants (by surgeon B and/or other surgeons), it can be concluded these surgical characteristics, when performed together, generally result in a better surgical outcome. In other words, the set of surgical characteristics of a first incision blood vessel 100R, a scalpel angle of 45° and a scalpel speed of 3.0 $cms^{-1}$ are correlated together and with better surgical outcomes. Teaching surgeons to adopt this set of surgical characteristics may therefore lead to improved surgical outcomes.

In an example, a set of surgical characteristics are determined to be correlated with each other when the correlation coefficient is above a first predetermined threshold for a predetermined statistically significant number of surgeries. Furthermore, a set of correlated surgical characteristics is determined to be correlated with a particular surgical outcome (e.g. greater than or equal to +0.5 for a more beneficial set of surgical characteristics which should be encouraged or less than or equal −0.5 for a less beneficial set of surgical characteristics which should be discouraged) when the correlation coefficient is above a second predetermined threshold for a predetermined statistically significant number of surgeries. In an example, both the first and second correlation coefficient thresholds are set at 0.8 (although they do not necessarily have to be the same) and the predetermined number of surgeries is set at 500. The surgeries are performed by different surgeons and/or the same surgeon over time.

In an example, sets of surgical characteristics used in respective surgeries together with outcome scores for those surgeries may be used to train a neural network (implemented by the processor 202). The neural network can then be used predict the surgical outcome associated with any set of surgical characteristics provided as an input to it. For example, the characteristics mentioned in FIG. 3 for a plurality of surgeries (e.g. 500 real life surgeries) and the respective outcomes of those surgeries may be used to train the network (e.g. with 400 of the surgeries being used as a training set and the remaining 100 surgeries being used as a test set to optimise the neural network parameters). Once the network is trained, trail combinations of characteristic values (e.g. different combinations of first incision blood vessel, scalpel angle and scalpel speed) are input to the neural network and the neural network then outputs a predicted outcome score (e.g. one of −1, −0.5, 0, +0.5 and +1) using each combination. The trial combination of characteristics providing the best predicted outcome score may then form the basis of surgical training. The use of a neural network thus allows historical outcome data to be used to achieve an approximation of the set of surgical characteristics which optimises the outcome score. The neural network may take into account other input data such as preoperative patient data, genomic data, disease staging or general outcomes for all skilled surgeons, for example.

Figure 5:
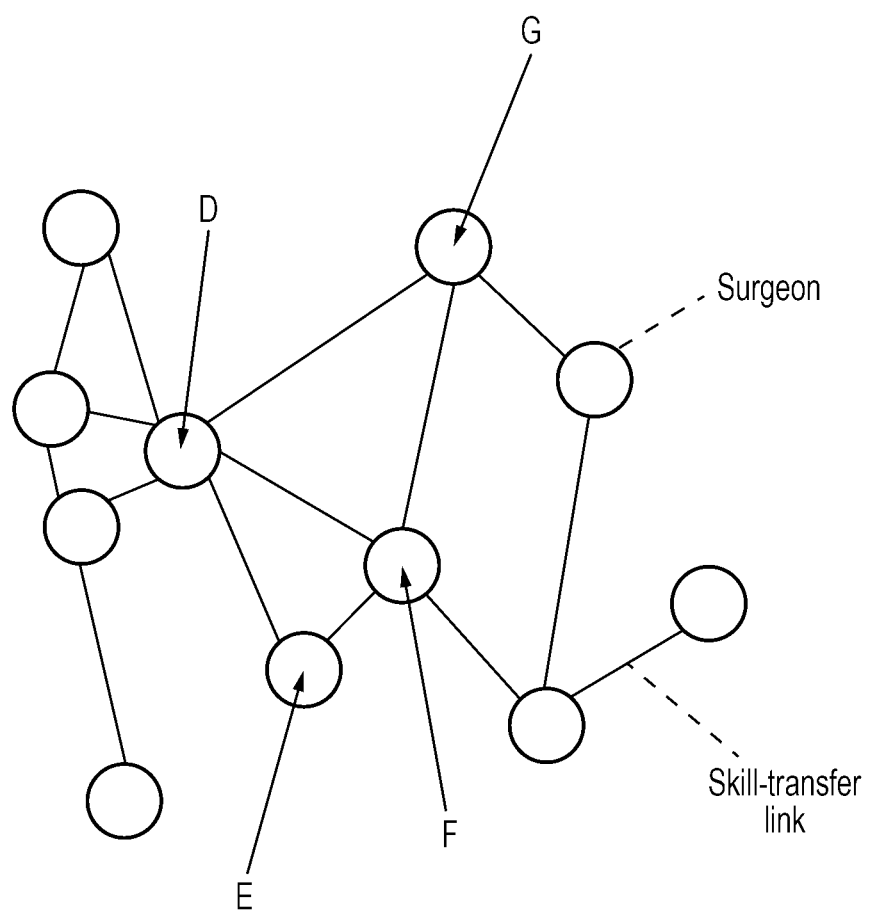
FIG. 5 shows a surgeon network.

FIG. 5 shows a network of surgeons (surgeon network). Each surgeon is represented by a node and links between nodes indicate a connection between surgeons. A link between two surgeons is based on those surgeons having something in common, such as being colleagues, having the same area of expertise or being part of the same surgical team, hospital department, hospital, hospital group, professional body, professional social network, training app community, medical school, historical mentor/mentee or student/teacher relationship or the like. Historical records of influence (see FIG. 6 for example) may also be used to establish a link between surgeons if no formal link exists (e.g. if, from recorded data of a changing surgical characteristic over time, one a surgeon looks to have influenced another surgeon a threshold number of times and/or for a threshold number of characteristics, a link can be established between those two surgeons).

Information identifying each surgeon (e.g. via a unique surgeon identifier such as a unique surgeon number) and which allows links between surgeons to be established (e.g. information identifying the surgical team, hospital department, etc. they are in) is stored in the storage medium 204. The links indicate possible skill transfer routes between surgeons. Surgeons often learn surgical techniques and characteristics from other surgeons they have a link with. The network of surgeons therefore provides information which surgeon potentially influences other surgeons. It is likely to be more beneficial to teach a set of surgical characteristics associated with a good outcome score to a surgeon with a higher level of influence. This is because it allows a small number of surgeons to be taught a set of surgical characteristics but for those surgical characteristics to then spread to many other surgeons. It is thought this is likely to be better than simply teaching all surgeons the set of surgical characteristics individually due to reduced time cost and because this better reflects the way in which junior surgeons are taught surgical techniques in the first place (much of surgical training involves watching surgery performed by a more experienced surgeon and performing surgery under supervision).

Establishing a network such as that of FIG. 5 thus helps to determine which surgeons might be a surgeon of influence and therefore which surgeons should be prioritised for training based on a new set of surgical characteristics. In particular, a surgeon with a large number of links to other surgeons might be more likely to be a surgeon of influence than a surgeon with only one or two links. However, it is desirable to have more information to determine the direction of influence of each surgeon in a surgical network. This is because the number of links a surgeon might not necessarily correspond to that surgeon's level of influence. It may just be, for example, that they are in several professional circles (and therefore have a large number of links) but are rarely influential on others. In fact, it might be that they themselves are influenced by a large number of other surgeons rather than being influential themselves. Training such a surgeon may therefore not be particularly effective for training of the surgical network as a whole.

In order to determine a surgeon of influence in the surgical network, other factors may therefore be considered. For example, each surgeon may be awarded a score which indicates their likely level of influence. This can be based on one or more factors in addition to the number of links they have. For example, a surgeons score may be higher if they have more years of experienced or if they are in a more senior position. This is still a relatively crude measure, however, since these factors are not necessarily always indicative of influence. The present technique therefore analyses the spread of surgical characteristics through the surgical network to determine a surgeon of influence more accurately. This is based on the principle that a surgical characteristics of an influential surgeon are likely to be passed on or copied by other surgeons with whom they are linked over time.

Figure 6:
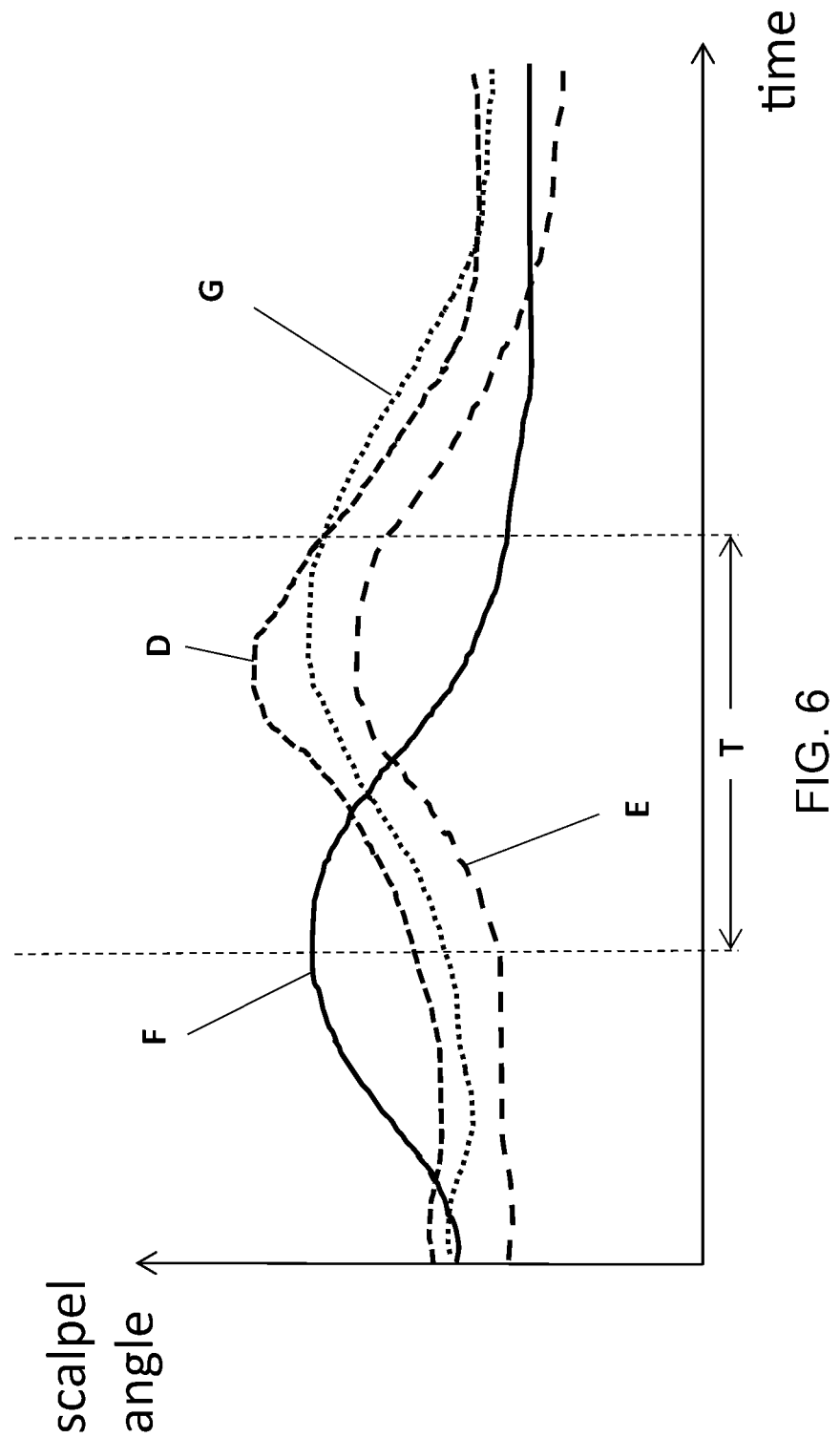
FIG. 6 shows a change in scalpel angle over time for different surgeons when making a first blood vessel incision in the surgical procedure of FIG. 2.

This is exemplified by FIG. 6 which shows the change in scalpel angle when making the first blood vessel incision (e.g. as in FIG. 2) during a liver transplant. It is often the case that a characteristic of a single surgeon varies over time as, for example, they read new medical literature or are simply guided by the experience. If this surgeon is a surgeon of influence, it is expected this change in characteristic will, in time, be mimicked by other surgeons linked to them. In FIG. 6, it can be seen that surgeon F in the network of FIG. 5 went through a period in which they increased the scalpel angle but then gradually reduced it until it was lower than it was initially. This could be due to, for example, the surgeon reading in medical literature that having a higher scalpel angle during the first blood vessel incision of a liver transplant is beneficial in some way but then finding this to be awkward in practice (resulting in them returning to a lower scalpel angle). This lead to a "peak" in scalpel angle for surgeon F. Within a time period T after this peak, each of surgeons D, E and G also experienced a "peak" in scalpel angle. This indicates that surgeon F is an influential surgeon in the network of FIG. 5. The scalpel angle for different liver transplants carried out by surgeons D, E, F and G over time is known because it is part of the surgical characteristic data collected over time to determine sets of correlated surgical characteristics associated with better surgical outcomes (as in FIG. 3, for example). Alternatively, a different characteristic from those used for assessing surgical outcomes may be used.

Reviewing the change in scalpel angle of different surgeons over time thus provides more information in determine the direction of influence in the network than the network alone. For example, looking at the network alone, all that can be ascertained is the number of links between surgeons. In this case, it might be determined that surgeon D has more influence than surgeon F since surgeon D has a higher number of links than surgeon F (six instead of five). However, the scalpel direction data indicates that, in fact, surgeon F is the most influential. Surgeon F is therefore the most appropriate surgeon to teach in order to improve the chance of surgical characteristics associated with better outcome scores being spread throughout the network.

Any number of factors, thresholds or the like can be used to determine an influential surgeon. This may be different for different surgical procedures. In an example, a surgeon is determined to be influential if they have at least a threshold number of links who are seen to mimic a change in at least one measured surgical characteristic within a certain time period. In FIG. 6, surgeon F would be determined as an influential surgeon if the threshold number of mimicking links was set at three (surgeons D, E and G), the certain period of time was set at T and the at least one measured surgical characteristic was set as the scalpel angle.

In an embodiment, additional information can be used to determine whether a surgeon is a surgeon of influence. For example, information indicating past training events in a surgeon's electronic calendar or past viewings of training videos in a surgeon's internet browser (with the surgeon's permission) may be received over a network (e.g. the internet or a hospital intranet) by the communication interface 201 and checked against changes in surgeon behaviour. In the example of FIG. 6, for example, if surgeons D, E and G are seen to have attended a training event or watched a training video relating to scalpel techniques shortly before the increase in scalpel angle for each of these surgeons shown in FIG. 6 was recorded, it may be that the increase in scalpel angle is a result of this training event or training video rather than a result of the influence of surgeon F. In this case, the surgeon F's level of influence may be reduced (e.g. by a predetermined number if the surgeon's level of influence is determined as a numerical level of influence—see below) since the link between the increase in scalpel angle of surgeon F and the increase in scalpel angle of surgeons D, E and G is less clear.

Figure 7:
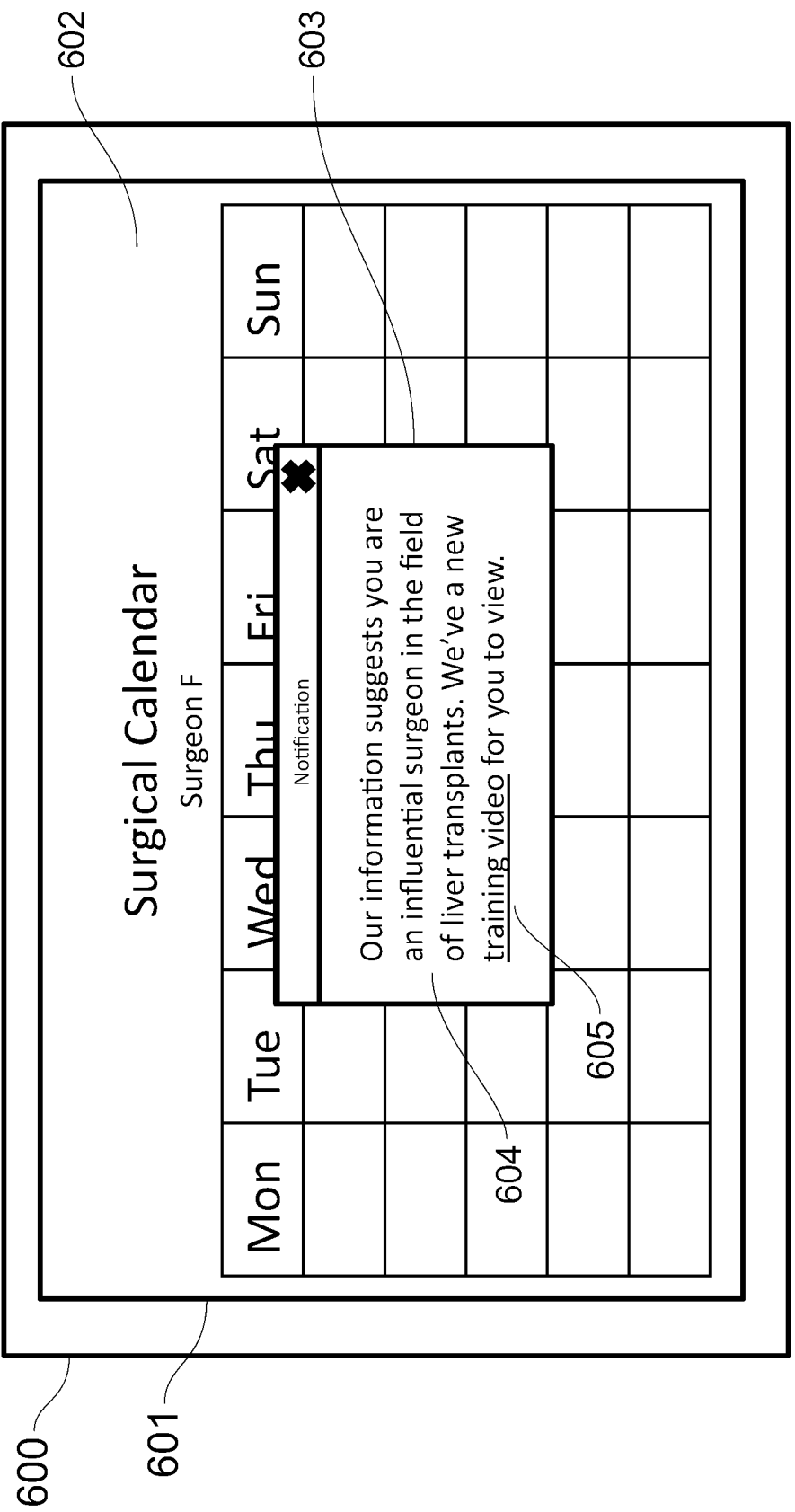
FIG. 7 shows an example information processing device of a surgeon.
Figure 8:
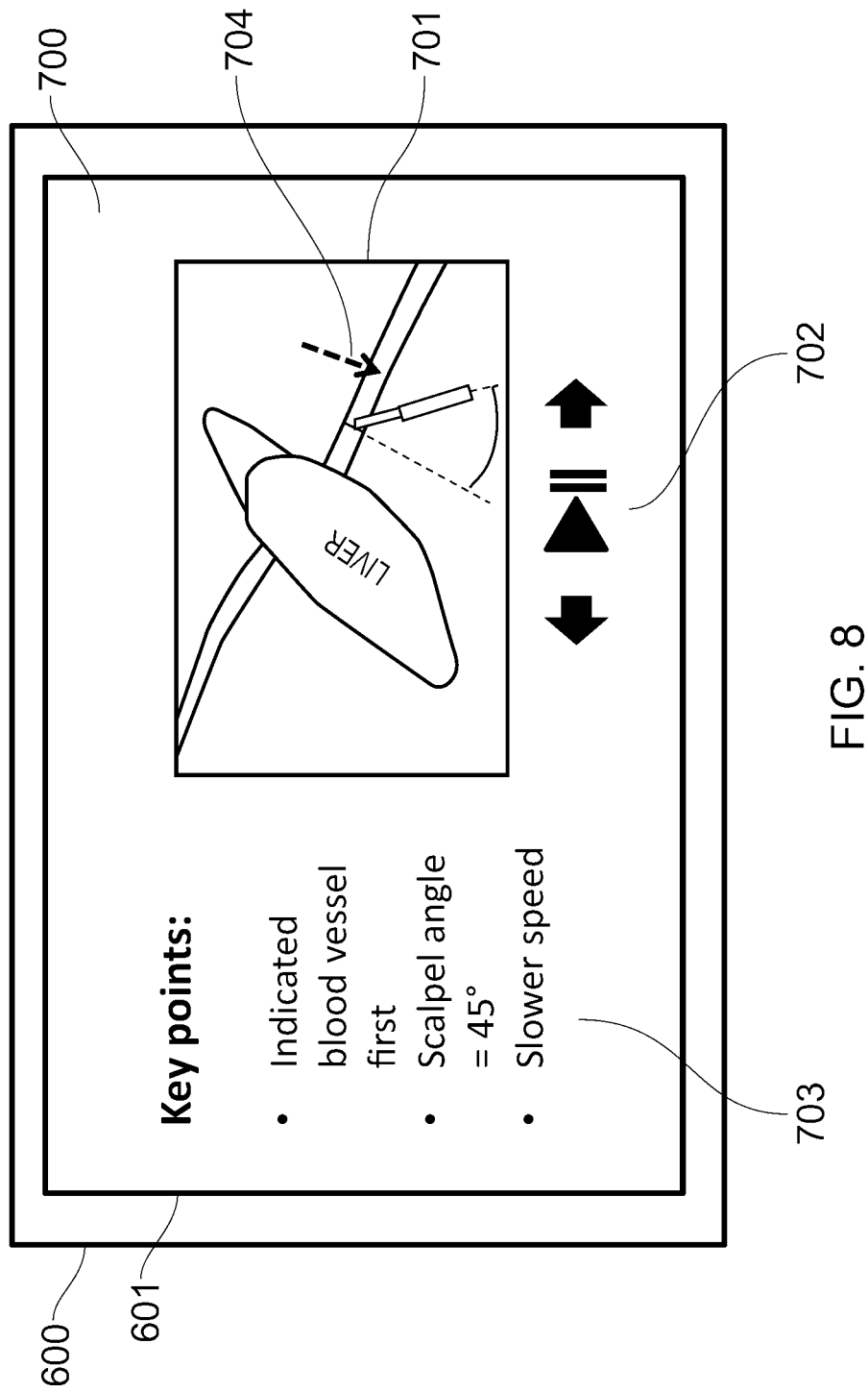
FIG. 8 shows an example interface for viewing a training video.

Once a surgeon has been determined as an influential surgeon, they may be selected for training. The training is intended to teach the surgeon the set of surgical characteristics for the surgical procedure (or part of it) which have been determined to lead to a better outcome score in the hope that the surgeon's influence will cause those characteristics to be propagated through the surgical network. The training may take any form. In the example of FIGS. 7 and 8, the training takes the form of a video. The video is made by a training provider based on the set of positive outcome characteristics. It is then distributed to the surgeon of influence so they can watch the video.

FIG. 7 shows an information processing device 600 to which a surgeon of influence has access. In this example, the device is a tablet computer comprising a touch screen 601. The tablet runs various applications (apps) used by the surgeon. In this case, a calendar app 602 is being run to show the surgeon scheduled surgeries and patient appointments. When a training video has been prepared by a training provider, this training video is stored in the storage medium 204 and an alert message is transmitted from the communication interface 201 to the tablet (e.g. over a computer network such as the internet or an internal hospital intranet). The alert message causes the touch screen to display a notification window 603. The notification window appears in front of the app the surgeon is currently using and comprises information 604 explaining that the surgeon has been determined to be an influential surgeon in the type of surgery concerned (in this case, liver transplants). The information 604 comprises selectable text 605 which, when selected by the surgeon, causes the training video to be played by the tablet. In an example, the selectable text is a hyperlink leading to the storage location of the video in the storage medium 204. The video is then streamed from the surgical training system to the tablet.

FIG. 8 shows an example interface 700 for viewing the streamed training video. The interface is that of a training app installed on the tablet 600 which opens in response to the surgeon selecting the selectable text 605 to view the training video. The interface comprises a video region 701 in which the training video is played. Touch screen controls 702 are selectable by the surgeon to play, pause, forward and rewind the video. The interface also comprises textual information 703 highlighting key points about the video. The textual information, in this case, highlights the surgical characteristics for the surgery carried out by surgeon B shown in FIG. 3 (which had the best outcome score). In particular, it indicates the first incision blood vessel (by means of animated arrow 704), the scalpel angle of 45° and that the scalpel speed should be slower. The scalpel speed message is determined based on a comparison between the desired scalpel speed (3.0 cms$^{-1}$ according to FIG. 3) and the recorded average first blood vessel incision scalpel speed of the surgeon in previous surgeries, for example. The provision of a comparative scalpel speed message (like "slower speed" in FIG. 8) rather than a numerical scalpel speed message (like "3.0 cms$^{-1}$") is more understandable to the surgeon. In this case, the message "slower speed" is given because the average scalpel speed of the surgeon is greater than 3.0 cms$^{-1}$. If the average scalpel speed of the surgeon were less than 3.0 cms$^{-1}$, a message such as "faster speed" would be given.

Once the surgeon of influence has been trained using the video, they are able to implement the training in the next surgeries they perform by adopting the characteristics emphasised in the video. This is likely to improve the outcome score of their future surgeries. Furthermore, their influence means that other surgeons (e.g. surgeons D, E and G when surgeon F is the surgeon of influence) are likely to pick up the characteristics, thereby allowing the characteristics and the associated improved surgical outcomes to propagate through the surgical network.

Different types of training (in addition to or instead of the surgical training video of FIG. 8, for example) are envisaged. For example, the training may be live training provided to the surgeon of influence. This could take the form of a seminar, podcast (or other form audio training), a hands on tuition session with an expert in the surgical field or an interactive training session with a surgical robot (if a surgical robot is used in the type of surgery concerned). In the latter case, the training may be provided in the form of exercises performed using a surgical robot simulator or an actual surgical robot in a training mode. For example, a training video may be displayed on a display of the surgical robot system and the user, whilst watching the training video, may be able to control a user interface of the surgical robot to practice what they are being taught by the training video in real time. This is applicable to a master-slave system, for example. The training may be personalised to the surgeon of influence (e.g. by looking at the historical surgical characteristics of the surgeon for the type of surgery concerned and focusing on those characteristics in need of most improvement to improve the outcome score).

The interface 700 may also comprise further types of digital training. For example, in addition to or instead of the text and video shown in FIG. 8, the interface may output audio, still images, digital surgical simulations, virtual reality (e.g. with additional required hardware such as a virtual reality headset (not shown) connected to the device 600) and/or augmented reality content to deliver training to the surgeon.

Digital surgical simulations take the form of an interactive surgical scenario presented using computer generated images which the surgeon can interact with by, for example, using the touch screen 601. For example, the surgeon may use the touch screen 601 to control a computer generated image of a scalpel to make an incision on a computer generated image of a patient. This may be combined with virtual and/or augmented reality as appropriate. This allows the surgeon to practice a surgical technique whenever they have access to device 600 (which can be virtually any time if the device 600 is a smartphone or tablet computer, for example) and potentially allows even better training than using the video or textual information of FIG. 8 due to the surgeon being able to virtually attempt surgical techniques and to obtain real time feedback on these techniques. Surgical characteristics and outcome information of past surgical performances can be used to develop suitable digital surgical simulations to encourage the adoption of surgical characteristics associated with better surgical outcomes.

In an embodiment, once training has been delivered to a surgeon of influence, the characteristics taught in the training are monitored over time together with the outcome values of surgeries to which they are applied (both by the surgeon of influence and surgeon(s) they are determined to influence). The effectiveness of the training can therefore be monitored and adjustments or updates to future training can be made as necessary.

Figure 9:
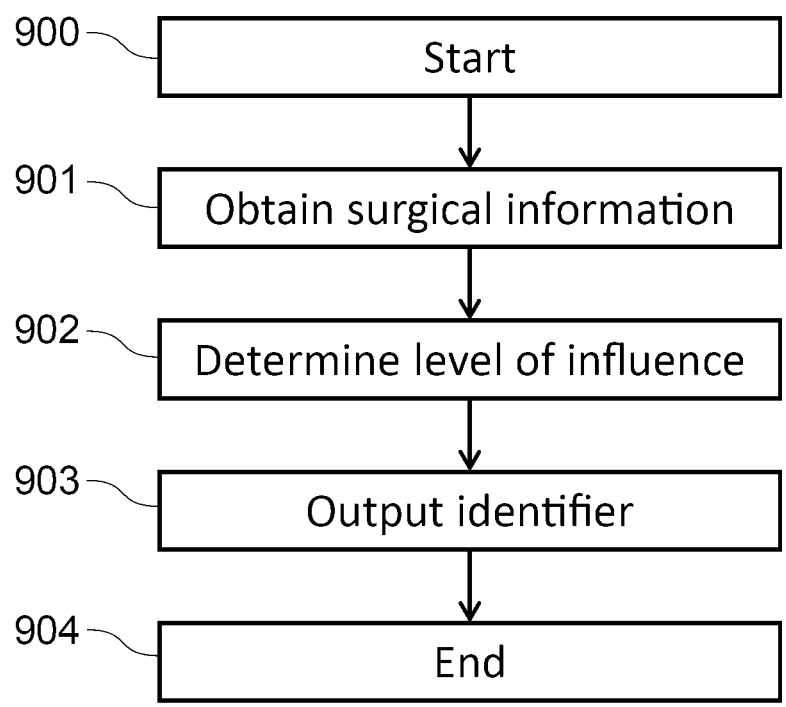
FIG. 9 shows a surgical training method according to an embodiment.

FIG. 9 shows a surgical training method carried out by the surgical training system 200 according to an embodiment. The method starts at step 900.

At step 901, the processor 202 obtains surgical information recorded during each of a plurality of surgeries (or, more generally, surgical performances) performed at a plurality of identified times by each of a plurality of surgeons in a surgeon network. The surgical information comprises one or more surgical characteristics of each surgeon (e.g. the first incision blood vessel, scalpel angle and/or scalpel speed of FIG. 3) for each surgery they perform, for example. The surgical information is obtained from one or more of a captured still image of the surgery, a captured video image of the surgery and surgical tool data (e.g. data output by a gyro sensor or accelerometer of a surgical tool or data indicative of a manufacturer, model and/or serial number of a surgical tool) received via the communication interface 201 and stored in the storage medium 204. The surgical information is stored as part of a database relating each surgeon (each surgeon having a unique surgeon identifier) with the surgeries they have performed (each surgery having a unique surgery identifier), the identified time of each surgery and the surgical characteristics of each surgery, for example. The identified time of each surgery comprises the date and time when the surgery occurred (e.g. based on a time stamp applied to data by the processor 202 as it is received at the communication interface 201), for example.

At step 902, the processor 202 determines a level of influence of each surgeon using the surgical information and the identified times. For example, in FIG. 6, the surgical information used is the characteristic of scalpel angle and the level of influence of each surgeon is determined based on how this changes for different surgeons at different times.

At step 903, the processor 202 outputs an identifier of a surgeon with a level of influence which meets a predetermined condition as a candidate for receiving training. In the example of FIG. 6, the processor 202 would output an identifier of surgeon F since surgeon F is determined to have the highest level of influence. The training is based on the surgical information and outcome information indicating a level of success of each of the plurality of surgeries. The training (e.g. in the form of a training video pushed to a device of the identified surgeon of influence—see FIGS. 7 and 8) recommends adoption of a combination of one or more surgical characteristics (e.g. the characteristics of surgeon B in FIG. 3) deemed to have a statistically significant correlation with an improved outcome score.

The method ends at step 904.

In the example of FIG. 6, surgeon F is determined to have a higher level of influence than the other surgeons they are connected to because a change in a single characteristic by surgeon F (scalpel angle in this case) appears to be mimicked by a number of other surgeons (surgeons D, E and G) whereas this is not the case for any of the other connected surgeons. In this case, there are two levels of influence. Surgeon F is at the higher level of influence whereas the surgeons connected to surgeon F are at the lower level of influence. Surgeon F is therefore selected as the surgeon of influence because they meet the predetermined condition of having the highest level of influence. In practice, a plurality of factors (influence factors) may contribute to the level of influence of each surgeon. Some example influence factors are now given.

A first example influence factor for each surgeon is a time of a change of a characteristic of the surgery determined by the surgeon relative to the time of a corresponding change of the characteristic by one or more other surgeons. It is determined if the corresponding change of the characteristic by the one or more other surgeons occurs at a time after and within a determined time period of the time of change of the characteristic by the surgeon. This is the case in the example of FIG. 6, in which the peak in scalpel angle occurs for surgeons D, E and G after the peak for surgeon F and within the time period T.

A second example influence factor for each surgeon is the number of other surgeons with a corresponding change of a characteristic occurring at a time after a time of change of the characteristic by the surgeon. It is determined if a threshold number of other surgeons with a corresponding change of the characteristic is met. In the example of FIG. 6, this would be met if the threshold is three or less (corresponding to surgeons D, E and F).

A third example influence factor each surgeon is the number of characteristics with a corresponding change by one or more other surgeons occurring at a time after a time of change of each of those characteristics by the surgeon. It is determined if a threshold number of characteristics with a corresponding change is met. In the example of FIG. 6, only one characteristic is considered (scalpel angle). However, a plurality of characteristics could be considered (e.g. first incision blood vessel and/or scalpel speed in addition to scalpel angle).

Other influence factors such as the number of connections a surgeon has in the network and their number of years of experience (this being stored in storage medium 204 as additional data in a database relating each unique surgeon identifier with the number of years of experience of that surgeon, for example) may also be taken into account.

A surgeon's level of influence may be determined by a combination of influence factors. For example, a surgeon may be awarded a numerical level of influence in which the number is increased the higher the number of factor thresholds which are met. Thus, for example, if the factor thresholds are that a surgeon's influence (e.g. that of surgeon F) must be seen by changes in at least two surgical characteristics (e.g. two of first incision blood vessel, scalpel angle and scalpel speed) for at least two other surgeons (e.g. two of surgeons D, E and G) within a determined time period T, the surgeon may be awarded one point per met threshold. Thus, a first surgeon who is seen to cause influence in a single characteristic for two other surgeons within time period T and second surgeon who is seen to cause influence in two characteristics for a single other surgeon within time period T will each be awarded two points (one point for the influence within time T and one point for meeting the surgeon number and characteristic number threshold, respectively). On the other hand, a third surgeon who is seen to cause influence in two characteristics for two other surgeons will be awarded three points (one point for the influence within time T, one point for meeting the surgeon number threshold and one point for meeting the characteristic number threshold). The third surgeon will thus be determined the most influential and therefore a surgeon of influence.

In this case, the third surgeon meets the predetermined condition of having the highest numerical level of influence (i.e. the highest number of points). Alternatively, the predetermined condition may be that at least a threshold number of point is met. This allows multiple surgeons to be determined as surgeons of influence and provided with training. For example, if the threshold number of points is set at two, the first, second and third surgeons will all be selected as surgeons of influence. However, another surgeon who only accrues one point, for example, will not be selected.

Additional points may be available for surgeons with at least a threshold number of network connections or with at least a threshold number of years of experience, for example. These are only examples and the influence factors and the way they are used to calculate the level of influence of a surgeon may vary for different types of surgery based on the expertise of the medical community.

In an embodiment, each surgeon in the network may also be associated with a surgical training and/or experience rating. For example, this can simply be the number of years of experience of the surgeon (e.g. starting from the time at which each surgeon obtained the qualification(s) necessary for them to conduct surgical procedures) or may be a more comprehensive number that takes into account a plurality of factors (e.g. an overall score based on the number of years of experience, number of surgical procedures completed and number and quality of qualifications). The surgeon network may also include trainee surgeons who are in the process of obtaining the necessary qualification(s) to practice.

In this case, as well as a surgeon of influence being given training, the training may also be delivered to all surgeons and/or trainees with a surgical training and/or experience rating less than a determined level. Although these surgeons and/or trainees aren't necessarily influential in the surgeon network, the lower surgical training and/or experience rating indicates they are likely to personally benefit most from additional training (especially training which focusses on surgical characteristics shown to be associated with better surgical outcomes). Sub-networks within the surgeon network made up of members of the surgeon network with certain characteristics, e.g. surgeons with a surgical training and/or experience rating less than the predetermined level, may also be determined. Members of the sub-network who are particularly influential (but who might not be as influential in the full surgeon network) may then be identified as candidates for training.

Thus, as well as the surgical training system 200 outputting an identifier of a surgeon as a candidate for training when that surgeon is determined as influential in the full surgeon network, identifiers of surgeons and/or trainees with surgical training and/or experience ratings less than a determined level (either all such surgeons and/or trainees or those deemed influential in a sub-network) may also be output as candidates for training.

The present technique therefore enables surgical characteristics associated with better surgical outcomes to be taught to surgeons in a network. Furthermore, this is achieved in an efficient and effective manner by focusing the teaching on surgeons more likely to influence other surgeons in the network.

Figure 10:
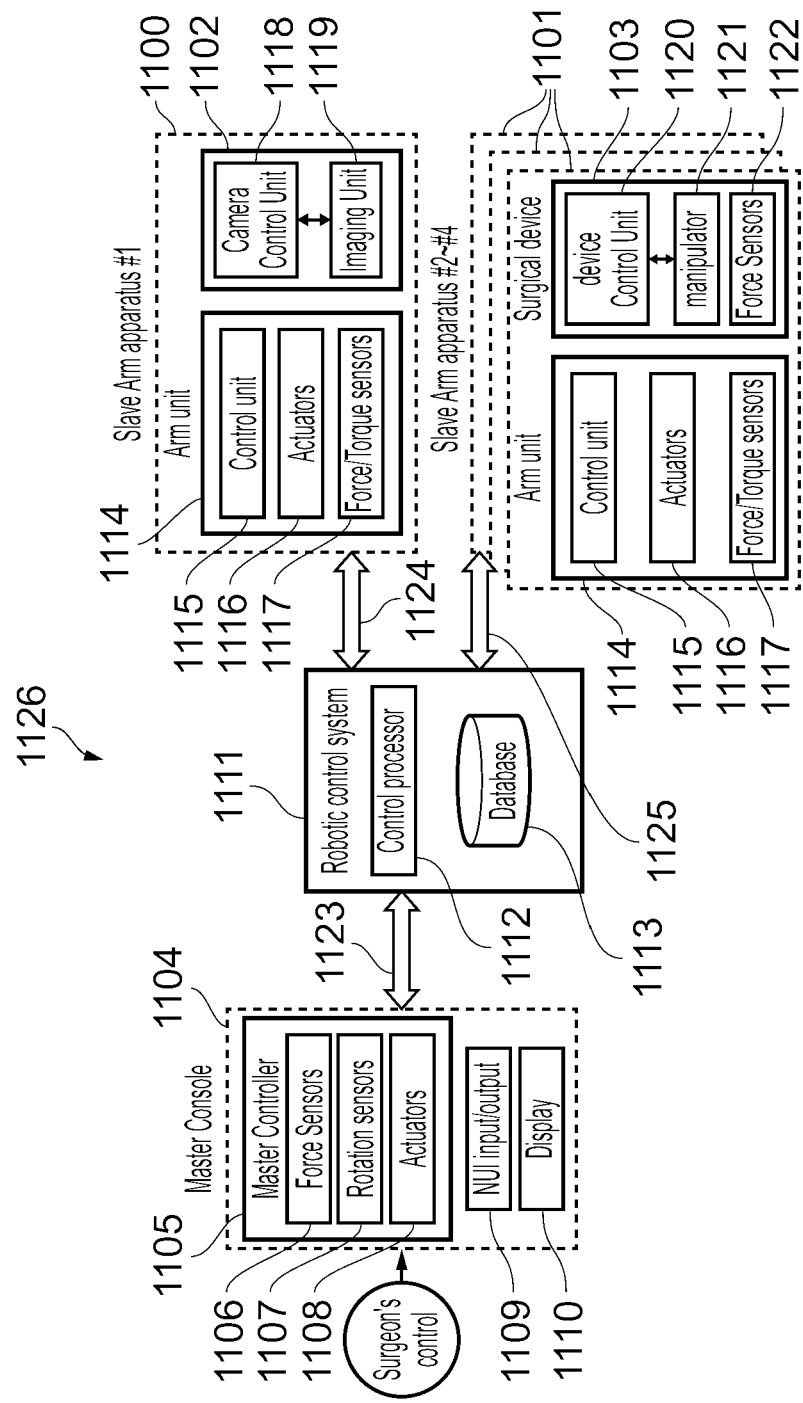
FIG. 10 shows a first example of a computer assisted surgery system to which the present technique is applicable.

FIG. 10 schematically shows an example of a computer assisted surgery system 1126 to which the present technique is applicable. The computer assisted surgery system is a master-slave (master slave) system incorporating an autonomous arm 1100 and one or more surgeon controlled arms 1101. The autonomous arm holds an imaging device 1102 (e.g. a surgical camera or medical vision scope such as a medical endoscope, surgical microscope or surgical exoscope). The one or more surgeon-controlled arms 1101 each hold a surgical device 1103 (e.g. a cutting tool or the like). The imaging device of the autonomous arm outputs an image of the surgical scene to an electronic display 1110 viewable by the surgeon. The autonomous arm autonomously adjusts the view of the imaging device whilst the surgeon performs the surgery using the one or more surgeon-controlled arms to provide the surgeon with an appropriate view of the surgical scene in real time.

The surgeon controls the one or more surgeon-controlled arms 1101 using a master console 1104. The master console includes a master controller 1105. The master controller 1105 includes one or more force sensors 1106 (e.g. torque sensors), one or more rotation sensors 1107 (e.g. encoders) and one or more actuators 1108. The master console includes an arm (not shown) including one or more joints and an operation portion. The operation portion can be grasped by the surgeon and moved to cause movement of the arm about the one or more joints. The one or more force sensors 1106 detect a force provided by the surgeon on the operation portion of the arm about the one or more joints. The one or more rotation sensors detect a rotation angle of the one or more joints of the arm. The actuator 1108 drives the arm about the one or more joints to allow the arm to provide haptic feedback to the surgeon. The master console includes a natural user interface (NUI) input/output for receiving input information from and providing output information to the surgeon. The NUI input/output includes the arm (which the surgeon moves to provide input information and which provides haptic feedback to the surgeon as output information). The NUI input/output may also include voice input, line of sight input and/or gesture input, for example. The master console comprises the electronic display 1110 for outputting images captured by the imaging device 1102.

The master console 1104 communicates with each of the autonomous arm 1100 and one or more surgeon-controlled arms 1101 via a robotic control system 1111. The robotic control system is connected to the master console 1104, autonomous arm 1100 and one or more surgeon-controlled arms 1101 by wired or wireless connections 1123, 1124 and 1125. The connections 1123, 1124 and 1125 allow the exchange of wired or wireless signals between the master console, autonomous arm and one or more surgeon-controlled arms.

The robotic control system includes a control processor 1112 and a database 1113. The control processor 1112 processes signals received from the one or more force sensors 1106 and one or more rotation sensors 1107 and outputs control signals in response to which one or more actuators 1116 drive the one or more surgeon controlled arms 1101. In this way, movement of the operation portion of the master console 1104 causes corresponding movement of the one or more surgeon controlled arms.

The control processor 1112 also outputs control signals in response to which one or more actuators 1116 drive the autonomous arm 1100. The control signals output to the autonomous arm are determined by the control processor 1112 in response to signals received from one or more of the master console 1104, one or more surgeon-controlled arms 1101, autonomous arm 1100 and any other signal sources (not shown). The received signals are signals which indicate an appropriate position of the autonomous arm for images with an appropriate view to be captured by the imaging device 1102. The database 1113 stores values of the received signals and corresponding positions of the autonomous arm.

For example, for a given combination of values of signals received from the one or more force sensors 1106 and rotation sensors 1107 of the master controller (which, in turn, indicate the corresponding movement of the one or more surgeon-controlled arms 1101), a corresponding position of the autonomous arm 1100 is set so that images captured by the imaging device 1102 are not occluded by the one or more surgeon-controlled arms 1101.

As another example, if signals output by one or more force sensors 1117 (e.g. torque sensors) of the autonomous arm indicate the autonomous arm is experiencing resistance (e.g. due to an obstacle in the autonomous arm's path), a corresponding position of the autonomous arm is set so that images are captured by the imaging device 1102 from an alternative view (e.g. one which allows the autonomous arm to move along an alternative path not involving the obstacle).

It will be appreciated there may be other types of received signals which indicate an appropriate position of the autonomous arm.

The control processor 1112 looks up the values of the received signals in the database 1112 and retrieves information indicating the corresponding position of the autonomous arm 1100. This information is then processed to generate further signals in response to which the actuators 1116 of the autonomous arm cause the autonomous arm to move to the indicated position.

Each of the autonomous arm 1100 and one or more surgeon-controlled arms 1101 includes an arm unit 1114. The arm unit includes an arm (not shown), a control unit 1115, one or more actuators 1116 and one or more force sensors 1117 (e.g. torque sensors). The arm includes one or more links and joints to allow movement of the arm. The control unit 1115 sends signals to and receives signals from the robotic control system 1111.

In response to signals received from the robotic control system, the control unit 1115 controls the one or more actuators 1116 to drive the arm about the one or more joints to move it to an appropriate position. For the one or more surgeon-controlled arms 1101, the received signals are generated by the robotic control system based on signals received from the master console 1104 (e.g. by the surgeon controlling the arm of the master console). For the autonomous arm 1100, the received signals are generated by the robotic control system looking up suitable autonomous arm position information in the database 1113.

In response to signals output by the one or more force sensors 1117 about the one or more joints, the control unit 1115 outputs signals to the robotic control system. For example, this allows the robotic control system to send signals indicative of resistance experienced by the one or more surgeon-controlled arms 1101 to the master console 1104 to provide corresponding haptic feedback to the surgeon (e.g. so that a resistance experienced by the one or more surgeon-controlled arms results in the actuators 1108 of the master console causing a corresponding resistance in the arm of the master console). As another example, this allows the robotic control system to look up suitable autonomous arm position information in the database 1113 (e.g. to find an alternative position of the autonomous arm if the one or more force sensors 1117 indicate an obstacle is in the path of the autonomous arm).

The imaging device 1102 of the autonomous arm 1100 includes a camera control unit 1118 and an imaging unit 1119. The camera control unit controls the imaging unit to capture images and controls various parameters of the captured image such as zoom level, exposure value, white balance and the like. The imaging unit captures images of the surgical scene. The imaging unit includes all components necessary for capturing images including one or more lenses and an image sensor (not shown). The view of the surgical scene from which images are captured depends on the position of the autonomous arm.

The surgical device 1103 of the one or more surgeon-controlled arms includes a device control unit 1120, manipulator 1121 (e.g. including one or more motors and/or actuators) and one or more force sensors 1122 (e.g. torque sensors).

The device control unit 1120 controls the manipulator to perform a physical action (e.g. a cutting action when the surgical device 1103 is a cutting tool) in response to signals received from the robotic control system 1111. The signals are generated by the robotic control system in response to signals received from the master console 1104 which are generated by the surgeon inputting information to the NUI input/output 1109 to control the surgical device. For example, the NUI input/output includes one or more buttons or levers comprised as part of the operation portion of the arm of the master console which are operable by the surgeon to cause the surgical device to perform a predetermined action (e.g. turning an electric blade on or off when the surgical device is a cutting tool).

The device control unit 1120 also receives signals from the one or more force sensors 1122. In response to the received signals, the device control unit provides corresponding signals to the robotic control system 1111 which, in turn, provides corresponding signals to the master console 1104. The master console provides haptic feedback to the surgeon via the NUI input/output 1109. The surgeon therefore receives haptic feedback from the surgical device 1103 as well as from the one or more surgeon-controlled arms 1101. For example, when the surgical device is a cutting tool, the haptic feedback involves the button or lever which operates the cutting tool to give greater resistance to operation when the signals from the one or more force sensors 1122 indicate a greater force on the cutting tool (as occurs when cutting through a harder material, e.g. bone) and to give lesser resistance to operation when the signals from the one or more force sensors 1122 indicate a lesser force on the cutting tool (as occurs when cutting through a softer material, e.g. muscle). The NUI input/output 1109 includes one or more suitable motors, actuators or the like to provide the haptic feedback in response to signals received from the robot control system 1111.

Figure 11:
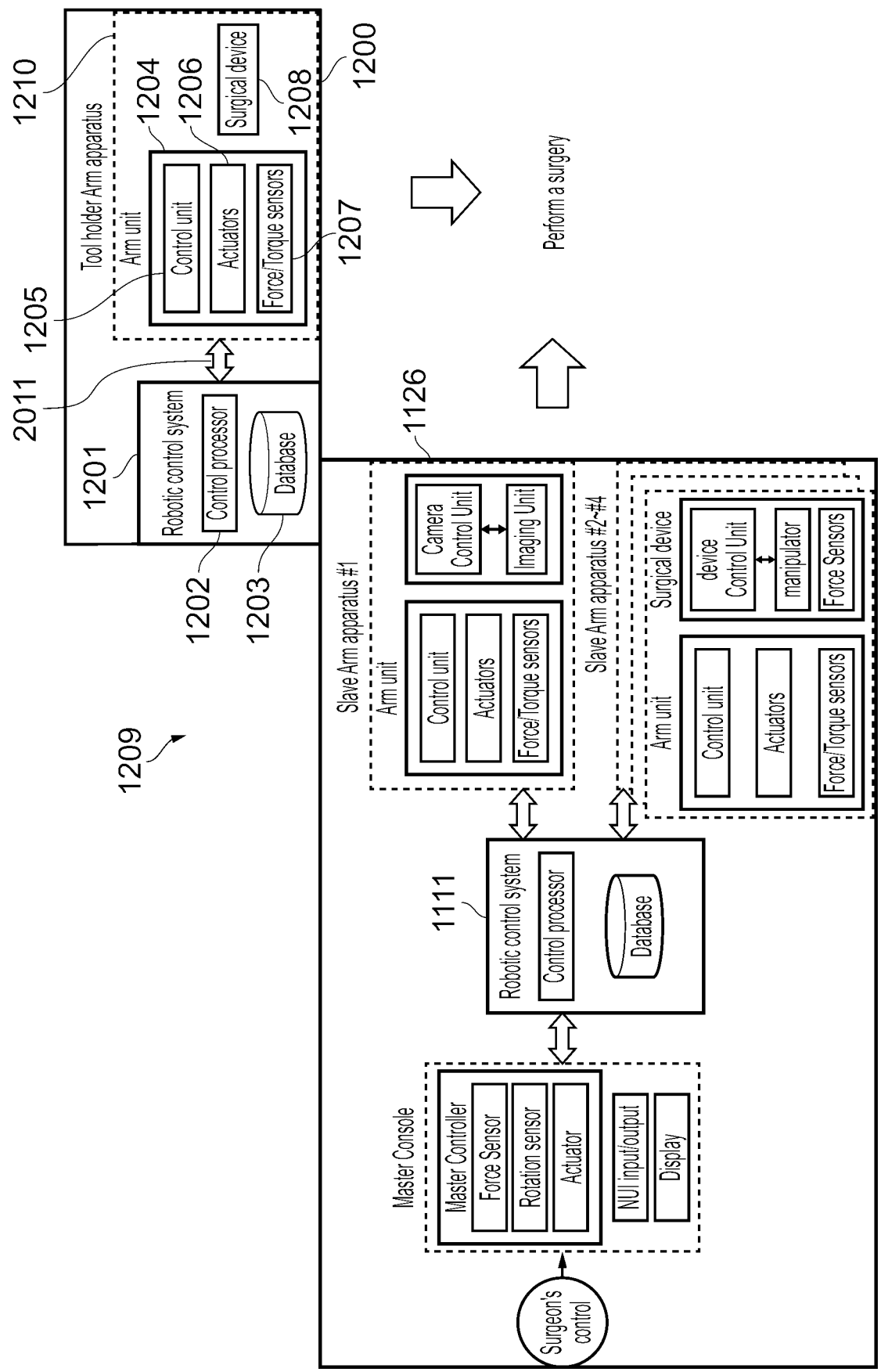
FIG. 11 shows a second example of a computer assisted surgery system to which the present technique is applicable.

FIG. 11 schematically shows another example of a computer assisted surgery system 1209 to which the present technique is applicable. The computer assisted surgery system 1209 is a surgery system in which the surgeon performs tasks via the master-slave system 1126 and a computerised surgical apparatus 1200 performs tasks autonomously.

The master-slave system 1126 is the same as FIG. 10 and is therefore not described. The master-slave system may, however, be a different system to that of FIG. 10 in alternative embodiments or may be omitted altogether (in which case the system 1209 works autonomously whilst the surgeon performs conventional surgery).

The computerised surgical apparatus 1200 includes a robotic control system 1201 and a tool holder arm apparatus 1210. The tool holder arm apparatus 1210 includes an arm unit 1204 and a surgical device 1208. The arm unit includes an arm (not shown), a control unit 1205, one or more actuators 1206 and one or more force sensors 1207 (e.g. torque sensors). The arm comprises one or more joints to allow movement of the arm. The tool holder arm apparatus 1210 sends signals to and receives signals from the robotic control system 1201 via a wired or wireless connection 1211. The robotic control system 1201 includes a control processor 1202 and a database 1203. Although shown as a separate robotic control system, the robotic control system 1201 and the robotic control system 1111 may be one and the same. The surgical device 1208 has the same components as the surgical device 1103. These are not shown in FIG. 11.

In response to control signals received from the robotic control system 1201, the control unit 1205 controls the one or more actuators 1206 to drive the arm about the one or more joints to move it to an appropriate position. The operation of the surgical device 1208 is also controlled by control signals received from the robotic control system 1201. The control signals are generated by the control processor 1202 in response to signals received from one or more of the arm unit 1204, surgical device 1208 and any other signal sources (not shown). The other signal sources may include an imaging device (e.g. imaging device 1102 of the master-slave system 1126) which captures images of the surgical scene. The values of the signals received by the control processor 1202 are compared to signal values stored in the database 1203 along with corresponding arm position and/or surgical device operation state information. The control processor 1202 retrieves from the database 1203 arm position and/or surgical device operation state information associated with the values of the received signals. The control processor 1202 then generates the control signals to be transmitted to the control unit 1205 and surgical device 1208 using the retrieved arm position and/or surgical device operation state information.

For example, if signals received from an imaging device which captures images of the surgical scene indicate a predetermined surgical scenario (e.g. via neural network image classification process or the like), the predetermined surgical scenario is looked up in the database 1203 and arm position information and/or surgical device operation state information associated with the predetermined surgical scenario is retrieved from the database. As another example, if signals indicate a value of resistance measured by the one or more force sensors 1207 about the one or more joints of the arm unit 1204, the value of resistance is looked up in the database 1203 and arm position information and/or surgical device operation state information associated with the value of resistance is retrieved from the database (e.g. to allow the position of the arm to be changed to an alternative position if an increased resistance corresponds to an obstacle in the arm's path). In either case, the control processor 1202 then sends signals to the control unit 1205 to control the one or more actuators 1206 to change the position of the arm to that indicated by the retrieved arm position information and/or signals to the surgical device 1208 to control the surgical device 1208 to enter an operation state indicated by the retrieved operation state information (e.g. turning an electric blade to an "on" state or "off" state if the surgical device 1208 is a cutting tool).

Figure 12:
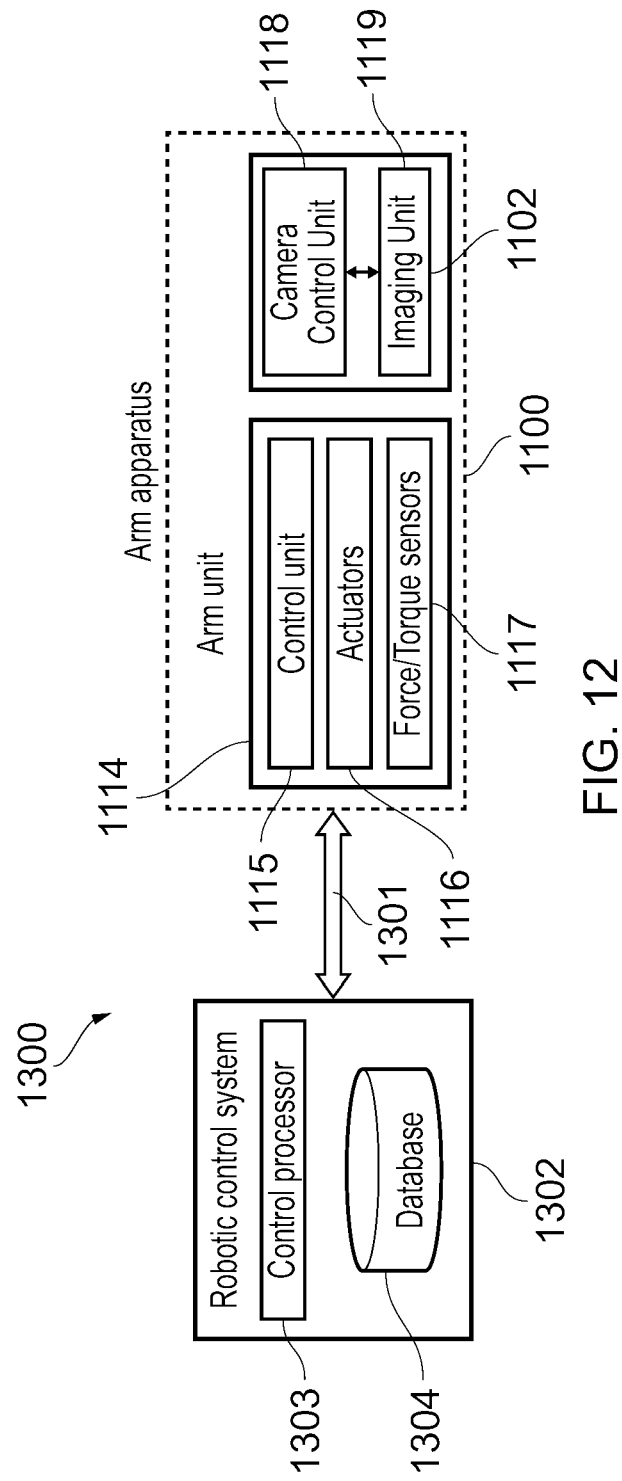
FIG. 12 shows a third example of a computer assisted surgery system to which the present technique is applicable.

FIG. 12 schematically shows another example of a computer assisted surgery system 1300 to which the present technique is applicable. The computer assisted surgery system 1300 is a computer assisted medical scope system in which an autonomous arm 1100 holds an imaging device 1102 (e.g. a medical scope such as an endoscope, microscope or exoscope). The imaging device of the autonomous arm outputs an image of the surgical scene to an electronic display (not shown) viewable by the surgeon. The autonomous arm autonomously adjusts the view of the imaging device whilst the surgeon performs the surgery to provide the surgeon with an appropriate view of the surgical scene in real time. The autonomous arm 1100 is the same as that of FIG. 10 and is therefore not described. However, in this case, the autonomous arm is provided as part of the stand-alone computer assisted medical scope system 1300 rather than as part of the master-slave system 1126 of FIG. 10. The autonomous arm 1100 can therefore be used in many different surgical setups including, for example, laparoscopic surgery (in which the medical scope is an endoscope) and open surgery.

The computer assisted medical scope system 1300 also includes a robotic control system 1302 for controlling the autonomous arm 1100. The robotic control system 1302 includes a control processor 1303 and a database 1304. Wired or wireless signals are exchanged between the robotic control system 1302 and autonomous arm 1100 via connection 1301.

In response to control signals received from the robotic control system 1302, the control unit 1115 controls the one or more actuators 1116 to drive the autonomous arm 1100 to move it to an appropriate position for images with an appropriate view to be captured by the imaging device 1102. The control signals are generated by the control processor 1303 in response to signals received from one or more of the arm unit 1114, imaging device 1102 and any other signal sources (not shown). The values of the signals received by the control processor 1303 are compared to signal values stored in the database 1304 along with corresponding arm position information. The control processor 1303 retrieves from the database 1304 arm position information associated with the values of the received signals. The control processor 1303 then generates the control signals to be transmitted to the control unit 1115 using the retrieved arm position information.

For example, if signals received from the imaging device 1102 indicate a predetermined surgical scenario (e.g. via neural network image classification process or the like), the predetermined surgical scenario is looked up in the database 1304 and arm position information associated with the predetermined surgical scenario is retrieved from the database. As another example, if signals indicate a value of resistance measured by the one or more force sensors 1117 of the arm unit 1114, the value of resistance is looked up in the database 1203 and arm position information associated with the value of resistance is retrieved from the database (e.g. to allow the position of the arm to be changed to an alternative position if an increased resistance corresponds to an obstacle in the arm's path). In either case, the control processor 1303 then sends signals to the control unit 1115 to control the one or more actuators 1116 to change the position of the arm to that indicated by the retrieved arm position information.

Figure 13:
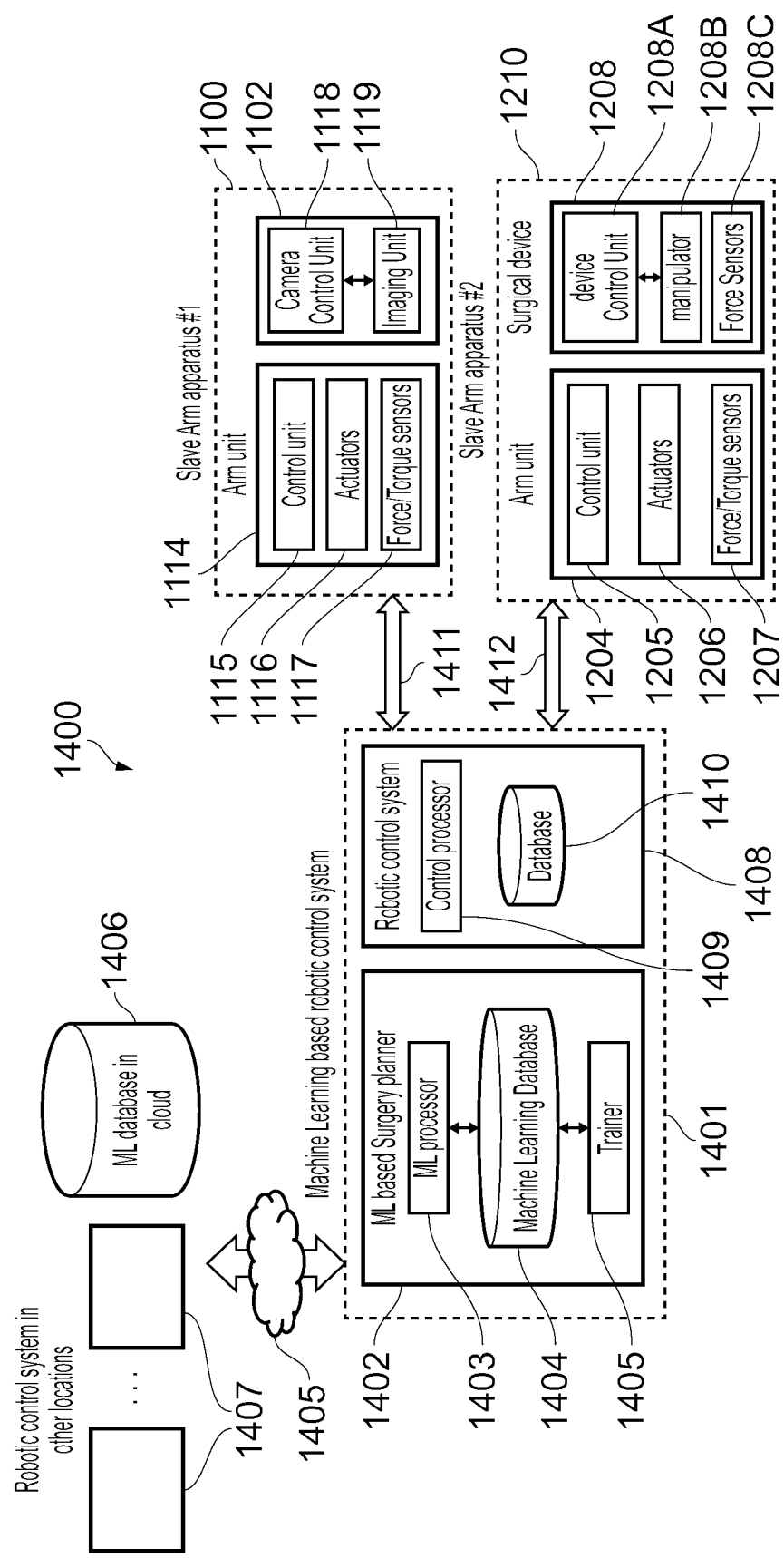
FIG. 13 shows a fourth example of a computer assisted surgery system to which the present technique is applicable.

FIG. 13 schematically shows another example of a computer assisted surgery system 1400 to which the present technique is applicable. The system includes one or more autonomous arms 1100 with an imaging unit 1102 and one or more autonomous arms 1210 with a surgical device 1210. The one or more autonomous arms 1100 and one or more autonomous arms 1210 are the same as those previously described. Each of the autonomous arms 1100 and 1210 is controlled by a robotic control system 1408 including a control processor 1409 and database 1410. Wired or wireless signals are transmitted between the robotic control system 1408 and each of the autonomous arms 1100 and 1210 via connections 1411 and 1412, respectively. The robotic control system 1408 performs the functions of the previously described robotic control systems 1111 and/or 1302 for controlling each of the autonomous arms 1100 and performs the functions of the previously described robotic control system 1201 for controlling each of the autonomous arms 1210.

The autonomous arms 1100 and 1210 perform at least a part of the surgery completely autonomously (e.g. when the system 1400 is an open surgery system). The robotic control system 1408 controls the autonomous arms 1100 and 1210 to perform predetermined actions during the surgery based on input information indicative of the current stage of the surgery and/or events happening in the surgery. For example, the input information includes images captured by the image capture device 1102. The input information may also include sounds captured by a microphone (not shown), detection of in-use surgical instruments based on motion sensors comprised with the surgical instruments (not shown) and/or any other suitable input information.

The input information is analysed using a suitable machine learning (ML) algorithm (e.g. a suitable artificial neural network) implemented by machine learning based surgery planning apparatus 1402. The planning apparatus 1402 includes a machine learning processor 1403, a machine learning database 1404 and a trainer 1405.

The machine learning database 1404 includes information indicating classifications of surgical stages (e.g. making an incision, removing an organ or applying stitches) and/or surgical events (e.g. a bleed or a patient parameter falling outside a predetermined range) and input information known in advance to correspond to those classifications (e.g. one or more images captured by the imaging device 1102 during each classified surgical stage and/or surgical event). The machine learning database 1404 is populated during a training phase by providing information indicating each classification and corresponding input information to the trainer 1405. The trainer 1405 then uses this information to train the machine learning algorithm (e.g. by using the information to determine suitable artificial neural network parameters). The machine learning algorithm is implemented by the machine learning processor 1403.

Once trained, previously unseen input information (e.g. newly captured images of a surgical scene) can be classified by the machine learning algorithm to determine a surgical stage and/or surgical event associated with that input information. The machine learning database also includes action information indicating the actions to be undertaken by each of the autonomous arms 1100 and 1210 in response to each surgical stage and/or surgical event stored in the machine learning database (e.g. controlling the autonomous arm 1210 to make the incision at the relevant location for the surgical stage "making an incision" and controlling the autonomous arm 1210 to perform an appropriate cauterisation for the surgical event "bleed"). The machine learning based surgery planner 1402 is therefore able to determine the relevant action to be taken by the autonomous arms 1100 and/or 1210 in response to the surgical stage and/or surgical event classification output by the machine learning algorithm. Information indicating the relevant action is provided to the robotic control system 1408 which, in turn, provides signals to the autonomous arms 1100 and/or 1210 to cause the relevant action to be performed.

The planning apparatus 1402 may be included within a control unit 1401 with the robotic control system 1408, thereby allowing direct electronic communication between the planning apparatus 1402 and robotic control system 1408. Alternatively or in addition, the robotic control system 1408 may receive signals from other devices 1407 over a communications network 1405 (e.g. the internet). This allows the autonomous arms 1100 and 1210 to be remotely controlled based on processing carried out by these other devices 1407. In an example, the devices 1407 are cloud servers with sufficient processing power to quickly implement complex machine learning algorithms, thereby arriving at more reliable surgical stage and/or surgical event classifications. Different machine learning algorithms may be implemented by different respective devices 1407 using the same training data stored in an external (e.g. cloud based) machine learning database 1406 accessible by each of the devices. Each device 1407 therefore does not need its own machine learning database (like machine learning database 1404 of planning apparatus 1402) and the training data can be updated and made available to all devices 1407 centrally. Each of the devices 1407 still includes a trainer (like trainer 1405) and machine learning processor (like machine learning processor 1403) to implement its respective machine learning algorithm.

Figure 14:
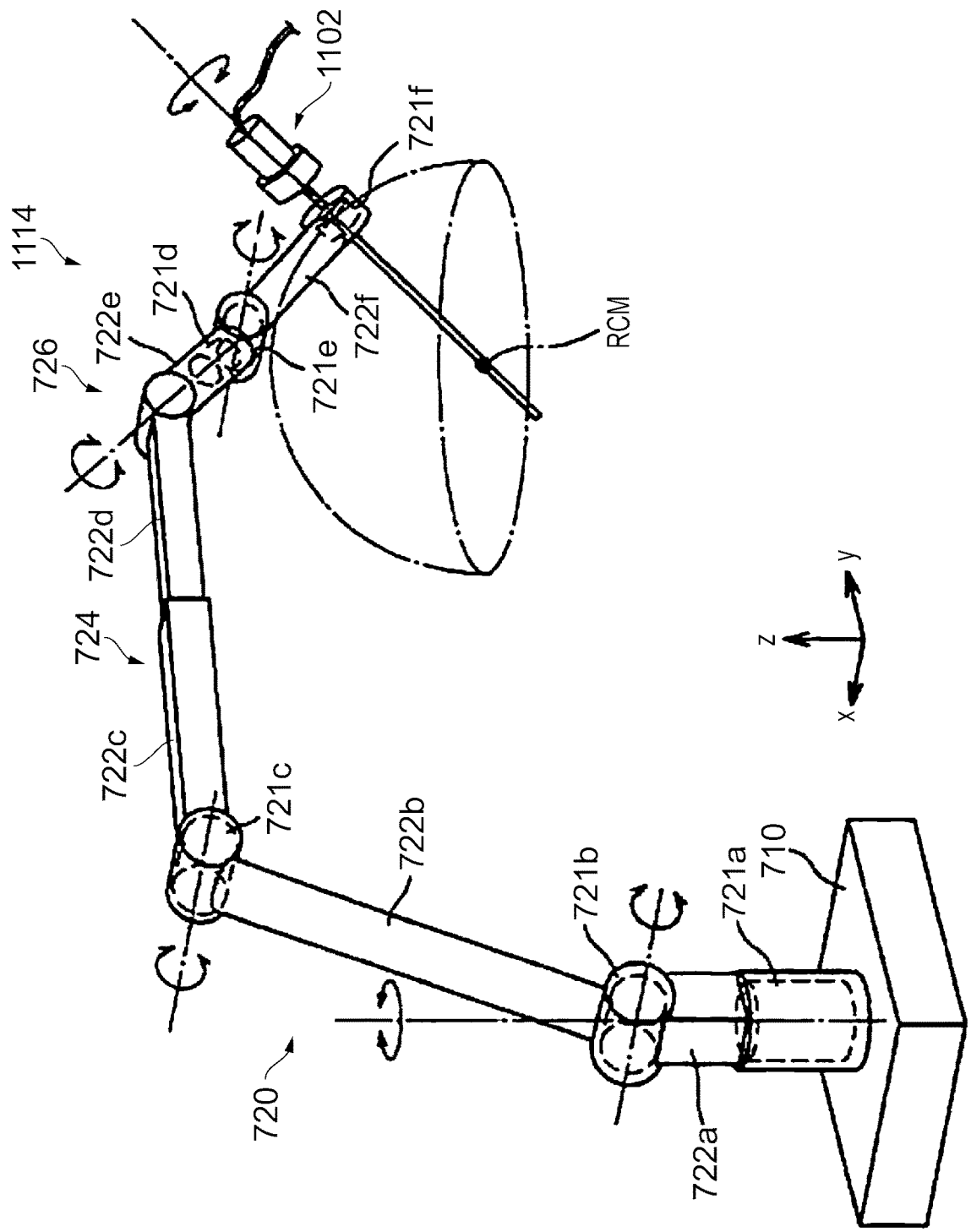
FIG. 14 shows an example of an arm unit.

FIG. 14 shows an example of the arm unit 1114. The arm unit 1204 is configured in the same way. In this example, the arm unit 1114 supports an endoscope as an imaging device 1102. However, in another example, a different imaging device 1102 or surgical device 1103 (in the case of arm unit 1114) or 1208 (in the case of arm unit 1204) is supported.

The arm unit 1114 includes a base 710 and an arm 720 extending from the base 710. The arm 720 includes a plurality of active joints 721a to 721f and supports the endoscope 1102 at a distal end of the arm 720. The links 722a to 722f are substantially rod-shaped members. Ends of the plurality of links 722a to 722f are connected to each other by active joints 721a to 721f, a passive slide mechanism 724 and a passive joint 726. The base unit 710 acts as a fulcrum so that an arm shape extends from the base 710.

A position and a posture of the endoscope 1102 are controlled by driving and controlling actuators provided in the active joints 721a to 721f of the arm 720. According to this example, a distal end of the endoscope 1102 is caused to enter a patient's body cavity, which is a treatment site, and captures an image of the treatment site. However, the endoscope 1102 may instead be another device such as another imaging device or a surgical device. More generally, a device held at the end of the arm 720 is referred to as a distal unit or distal device.

Here, the arm unit 1114 is described by defining coordinate axes as illustrated in FIG. 14 as follows. Furthermore, a vertical direction, a longitudinal direction, and a horizontal direction are defined according to the coordinate axes. In other words, a vertical direction with respect to the base 710 installed on the floor surface is defined as a z-axis direction and the vertical direction. Furthermore, a direction orthogonal to the z axis, the direction in which the arm 720 is extended from the base 710 (in other words, a direction in which the endoscope 1102 is positioned with respect to the base 710) is defined as a y-axis direction and the longitudinal direction. Moreover, a direction orthogonal to the y-axis and z-axis is defined as an x-axis direction and the horizontal direction.

The active joints 721a to 721f connect the links to each other to be rotatable. The active joints 721a to 721f have the actuators, and have each rotation mechanism that is driven to rotate about a predetermined rotation axis by drive of the actuator. As the rotational drive of each of the active joints 721a to 721f is controlled, it is possible to control the drive of the arm 720, for example, to extend or contract (fold) the arm 720.

The passive slide mechanism 724 is an aspect of a passive form change mechanism, and connects the link 722c and the link 722d to each other to be movable forward and rearward along a predetermined direction. The passive slide mechanism 724 is operated to move forward and rearward by, for example, a user, and a distance between the active joint 721c at one end side of the link 722c and the passive joint 726 is variable. With the configuration, the whole form of the arm 720 can be changed.

The passive joint 736 is an aspect of the passive form change mechanism, and connects the link 722d and the link 722e to each other to be rotatable. The passive joint 726 is operated to rotate by, for example, the user, and an angle formed between the link 722d and the link 722e is variable. With the configuration, the whole form of the arm 720 can be changed. In an embodiment, the arm unit 1114 has the six active joints 721a to 721f, and six degrees of freedom are realized regarding the drive of the arm 720. That is, the passive slide mechanism 726 and the passive joint 726 are not objects to be subjected to the drive control while the drive control of the arm unit 1114 is realized by the drive control of the six active joints 721a to 721f.

Specifically, as illustrated in FIG. 14 the active joints 721a, 721d, and 721f are provided so as to have each long axis direction of the connected links 722a and 722e and a capturing direction of the connected endoscope 1102 as a rotational axis direction. The active joints 721b, 721c, and 721e are provided so as to have the x-axis direction, which is a direction in which a connection angle of each of the connected links 722a to 722c, 722e, and 722f and the endoscope 1102 is changed within a y-z plane (a plane defined by the y axis and the z axis), as a rotation axis direction. In this manner, the active joints 721a, 721d, and 721f have a function of performing so-called yawing, and the active joints 721b, 721c, and 721e have a function of performing so-called pitching.

Since the six degrees of freedom are realized with respect to the drive of the arm 720 in the arm unit 1114, the endoscope 1102 can be freely moved within a movable range of the arm 720. FIG. 14 illustrates a hemisphere as an example of the movable range of the endoscope 723. Assuming that a central point RCM (remote centre of motion) of the hemisphere is a capturing centre of a treatment site captured by the endoscope 1102, it is possible to capture the treatment site from various angles by moving the endoscope 1102 on a spherical surface of the hemisphere in a state where the capturing centre of the endoscope 1102 is fixed at the centre point of the hemisphere.

Figure 15:
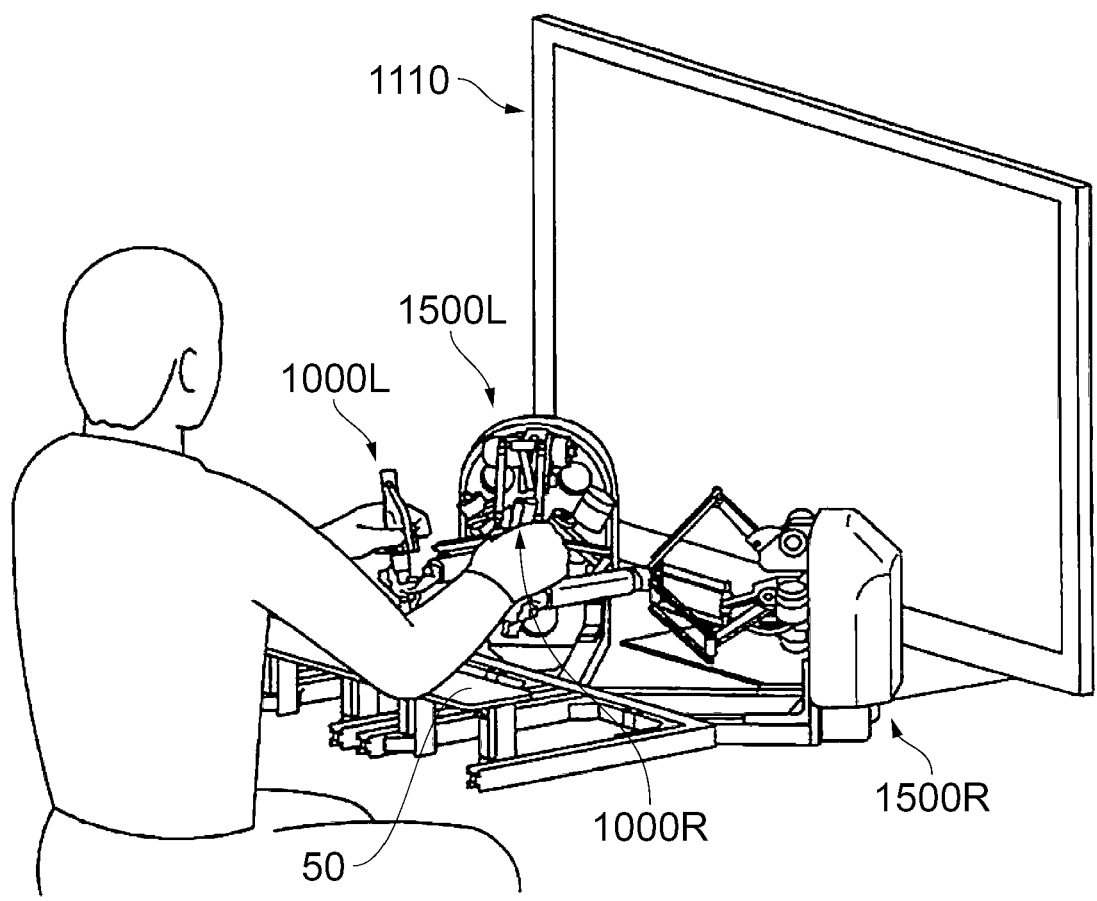
FIG. 15 shows an example of a master console.

FIG. 15 shows an example of the master console 1104. Two control portions 1500R and 1500L for a right hand and a left hand are provided. A surgeon puts both arms or both elbows on the supporting base 50, and uses the right hand and the left hand to grasp the operation portions 1000R and 1000L, respectively. In this state, the surgeon operates the operation portions 1000R and 1000L while watching electronic display 1110 showing a surgical site. The surgeon may displace the positions or directions of the respective operation portions 1000R and 1000L to remotely operate the positions or directions of surgical instruments attached to one or more slave apparatuses or use each surgical instrument to perform a grasping operation.

Figure 16:
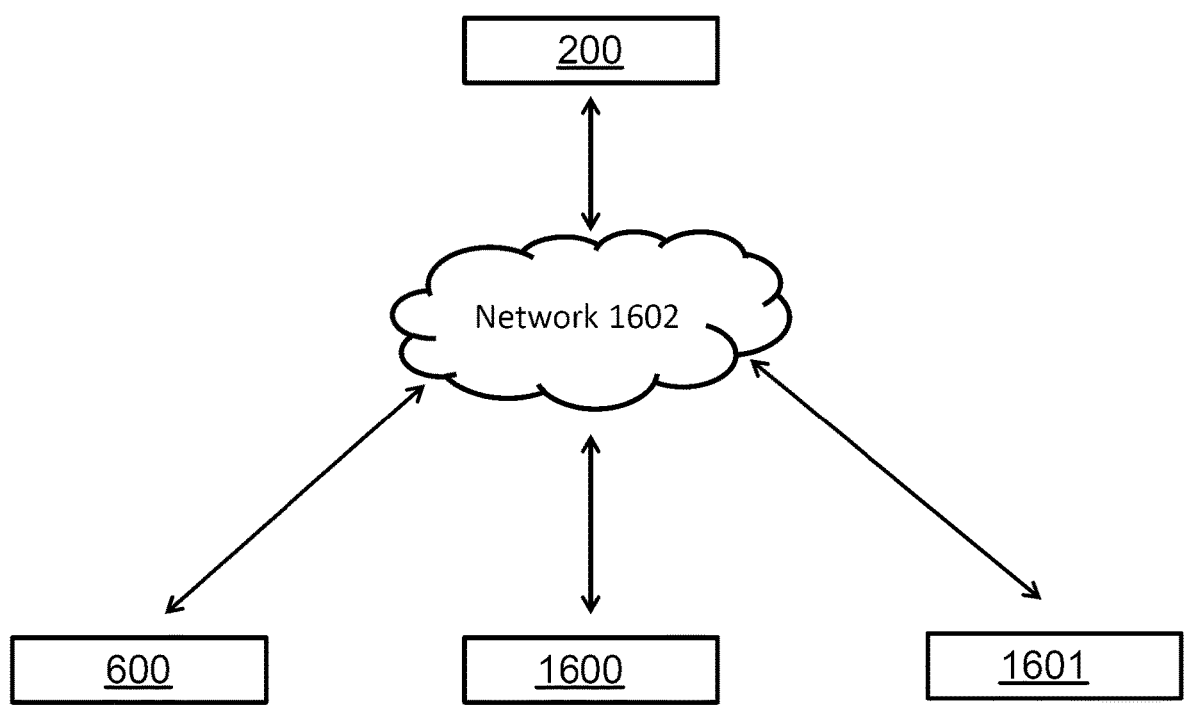
FIG. 16 shows an example system comprising a surgical training system, one or more information processing devices, one or more monitoring devices and a server according to an embodiment.

FIG. 16 shows a system in which the surgical training apparatus 200 may be implemented according to any embodiment. The system comprises the surgical training apparatus 200, one or more information processing devices 600 (each device 600 being e.g. a smartphone or tablet computer of a surgeon), one or more monitoring devices 1600 (each monitoring device being a device used to determine surgical characteristics during a surgical performance, e.g. a surgical camera outputting image data of a surgical performance or a surgical tool outputting surgical tool data obtained during a surgical performance) and a server 1601 connected via a network 1602. The network is the Internet or another Wide Area Network (WAN) or a Local Area Network (LAN), for example. In an embodiment, the network may be a Virtual Private Network such as a network run by a single entity, for example a set of training institutions or a company that hosts surgical training sessions. The surgical training apparatus 200 sends and receives data over the network 1602 via the communication interface 201.

The server 1601 is an information processing apparatus comprising circuitry and a storage medium (e.g. a hard disk drive, solid state drive or tape drive) configured to store the identifier of each surgeon and information about each surgeon. The information about each surgeon includes the identifier(s) of other surgeons the surgeon is connected to in the surgeon network. This allows the surgical training apparatus 200 to determine a surgeon of influence in a surgeon network even when information defining the surgeon network (i.e. the identifier of each surgeon in the network and the identifier(s) of the other surgeon(s) they are connected to) is stored at a different location (e.g. the server 1601 instead of the storage medium 204). The information about each surgeon also comprises information allowing digital training to be delivered to that surgeon if that surgeon is, for example, deemed to be a surgeon of influence. This information includes a unique identifier of a device 600 associated with the surgeon (e.g. a username or email address the surgeon uses to log in to an app to access the interface 700). When undertaking a surgical performance, the surgeon also indicates their unique surgeon identifier to the one or more monitoring devices 1600 (e.g. via a suitable user interface—not shown) so that surgical characteristic(s) associated with the surgical performance are associated with the surgeon. These are then stored (e.g. at the server 1601 and/or in the storage medium 204 of the surgical training apparatus 200).

The system of FIG. 16 therefore allows data indicative of surgical characteristics of a surgeon during a surgical performance to be gathered (by the one or more monitoring apparatuses 1600) and stored and associated with the unique identifier of that surgeon (in the storage medium 204 and/or server 1601). A surgeon of influence can then be determined using this information and using the surgeon network (defined by each surgeon identifier and its related surgeon identifier(s) by the server 1601) and digital training delivered to the identified surgeon of influence (via an information processing device 600 associated with that surgeon).

Some embodiments of the present technique are defined by the following numbered clauses:

(1)
A surgical training system comprising
circuitry configured to:
obtain surgical information recorded during each of a plurality of surgical performances occurring at a plurality of identified times by each of a plurality of surgeons in a surgeon network;
determine a level of influence of each surgeon using the surgical information and the identified times; and
output an identifier of a surgeon with a level of influence which meets a predetermined condition as a candidate for receiving training.

(2)
The surgical training system according to clause (1), wherein the training is based on the surgical information and outcome information indicating a level of success of each of the plurality of surgical performances.

(3)
The surgical training system according to clause (1), wherein the surgical information recorded during each of the plurality of surgical performances comprises a surgical characteristic of the surgeon.

(4)
The surgical training system according to clause (3), wherein the circuitry is configured to group a plurality of surgical characteristics which are correlated between surgeons and/or over time and associate the characteristic group with corresponding outcome information.

(5)
The surgical training system according to clause (3) or (4), wherein the level of influence of each surgeon is determined based on a time of a change of a surgical characteristic of the surgeon relative to the time of a corresponding change of the surgical characteristic by one or more other surgeons.

(6)
The surgical training system according to clause (5), wherein determining the level of influence of each surgeon comprises determining if a threshold number of other surgeons with a corresponding change of the surgical characteristic occurring at a time after the time of change of the surgical characteristic by the surgeon is met.

(7)
The surgical training system according to clause (5) or (6), wherein determining the level of influence of each surgeon comprises determining if a corresponding change of a threshold number of surgical characteristics by the one or more other surgeons at a time after the time of change of those surgical characteristics by the surgeon is met.

(8)
The surgical training system according to any one of clauses (5) to (7), wherein determining the level of influence of each surgeon comprises determining if a corresponding change of the surgical characteristic by the one or more other surgeons occurs at a time after and within a determined time period of the time of change of the surgical characteristic by the surgeon.

(9)
The surgical training system according to any one of clauses (3) to (8), wherein the circuitry is configured to run a neural network configured to receive input data indicating a plurality of surgical characteristics of the surgical performance and to output predicted outcome information for use in the training, the neural network being trained using historical surgical characteristics and associated outcome information.

(10)
The surgical training system according to any preceding clause, wherein each surgeon in the network is linked to at least one other surgeon in the network via a known existing association.

(11)
The surgical training system according to any preceding clause, wherein the surgical information recorded during each of the plurality of surgical performances is obtained from one or more of a captured still image of the surgical performance, a captured video image of the surgical performance and surgical tool data.

(12)

The surgical training system according to any preceding clause, wherein:
  each surgeon in the network is associated with a surgical training and/or experience rating; and
  the circuitry is configured to output an identifier of each surgeon with a surgical training and/or experience rating less than a determined level as a candidate for receiving training.

(13)

The surgical training system according to any preceding clause, wherein the training comprises digital training comprising one or more of text, audio, image, video, surgical simulation, virtual reality and augmented reality content delivered to a computing device of a surgeon.

(14)

A surgical training method comprising:
  obtaining surgical information recorded during each of a plurality of surgical performances occurring at a plurality of identified times by each of a plurality of surgeons in a surgeon network;
  determining a level of influence of each surgeon using the surgical information and the identified times; and
  outputting an identifier of a surgeon with a level of influence which meets a predetermined condition as a candidate for receiving training.

(15)

A program for controlling a computer to perform a method according to clause (14).

(16)

A storage medium storing a program according to clause (15).

Numerous modifications and variations of the present disclosure are possible in light of the above teachings. It is therefore to be understood that within the scope of the appended claims, the disclosure may be practiced otherwise than as specifically described herein.

In so far as embodiments of the disclosure have been described as being implemented, at least in part, by software-controlled data processing apparatus, it will be appreciated that a nontransitory machine-readable medium carrying such software, such as an optical disk, a magnetic disk, semiconductor memory or the like, is also considered to represent an embodiment of the present disclosure.

It will be appreciated that the above description for clarity has described embodiments with reference to different functional units, circuitry and/or processors. However, it will be apparent that any suitable distribution of functionality between different functional units, circuitry and/or processors may be used without detracting from the embodiments.

Described embodiments may be implemented in any suitable form including hardware, software, firmware or any combination of these. Described embodiments may optionally be implemented at least partly as computer software running on one or more data processors and/or digital signal processors. The elements and components of any embodiment may be physically, functionally and logically implemented in any suitable way. Indeed the functionality may be implemented in a single unit, in a plurality of units or as part of other functional units. As such, the disclosed embodiments may be implemented in a single unit or may be physically and functionally distributed between different units, circuitry and/or processors.

Although the present disclosure has been described in connection with some embodiments, it is not intended to be limited to the specific form set forth herein. Additionally, although a feature may appear to be described in connection with particular embodiments, one skilled in the art would recognize that various features of the described embodiments may be combined in any manner suitable to implement the technique.

The invention claimed is:

1. A surgical training system comprising
circuitry configured to:
  obtain surgical information recorded during each of a plurality of surgical performances occurring at a plurality of identified times by each of a plurality of surgeons in a surgeon network;
  determine a level of influence of each surgeon using the surgical information and the identified times;
  identify a surgeon with a level of influence which meets a predetermined condition as a candidate for receiving training;
  train the identified surgeon operating a master console on a surgery;
  monitor the identified surgeon using the master console during training on the surgery;
  supply signals output from the master console in response to manipulation by the identified surgeon during training to control a surgical arm including a surgical device, wherein the surgical arm is in communication with the master console; and
  supply signals from the surgical arm to the master console to provide haptic feedback to the identified surgeon during training.

2. The surgical training system according to claim 1, wherein the training is based on the surgical information and outcome information indicating a level of success of each of the plurality of surgical performances.

3. The surgical training system according to claim 1, wherein the surgical information recorded during each of the plurality of surgical performances comprises a surgical characteristic of the surgeon.

4. The surgical training system according to claim 3, wherein the circuitry is configured to group a plurality of surgical characteristics which are correlated between surgeons and/or over time and associate the characteristic group with corresponding outcome information.

5. The surgical training system according to claim 3, wherein the level of influence of each surgeon is determined based on a time of a change of a surgical characteristic of the surgeon relative to the time of a corresponding change of the surgical characteristic by one or more other surgeons.

6. The surgical training system according to claim 5, wherein determining the level of influence of each surgeon comprises determining if a threshold number of other surgeons with a corresponding change of the surgical characteristic occurring at a time after the time of change of the surgical characteristic by the surgeon is met.

7. The surgical training system according to claim 5, wherein determining the level of influence of each surgeon comprises determining if a corresponding change of a threshold number of surgical characteristics by the one or more other surgeons at a time after the time of change of those surgical characteristics by the surgeon is met.

8. The surgical training system according to claim 5, wherein determining the level of influence of each surgeon comprises determining if a corresponding change of the surgical characteristic by the one or more other surgeons occurs at a time after and within a determined time period of the time of change of the surgical characteristic by the surgeon.

9. The surgical training system according to claim 3, wherein the circuitry is configured to run a neural network configured to receive input data indicating a plurality of surgical characteristics of the surgical performance and to output predicted outcome information for use in the training, the neural network being trained using historical surgical characteristics and associated outcome information.

10. The surgical training system according to claim 1, wherein each surgeon in the network is linked to at least one other surgeon in the network via a known existing association.

11. The surgical training system according to claim 1, wherein the surgical information recorded during each of the plurality of surgical performances is obtained from one or more of a captured still image of the surgical performance, a captured video image of the surgical performance and surgical tool data.

12. The surgical training system according to claim 1, wherein:
 each surgeon in the network is associated with a surgical training and/or experience rating; and
 the circuitry is configured to output an identifier of each surgeon with a surgical training and/or experience rating less than a determined level as a candidate for receiving training.

13. The surgical training system according to claim 1, wherein the training comprises digital training comprising one or more of text, audio, image, video, surgical simulation, virtual reality and augmented reality content delivered to a computing device of a surgeon.

14. The surgical training system according to claim 1, wherein the circuitry is further configured to control an autonomous imaging arm including an image sensor so that an image output by the image sensor is not occluded by the surgical arm during training.

15. The surgical training system according to claim 14, wherein the circuitry is further configured to:
 determine if the autonomous imaging arm is subject to resistance; and
 in response to the autonomous imaging arm being subject to resistance, control the autonomous imaging arm so that an image output by the image sensor is from a view allowing free movement of the autonomous imaging arm.

16. A surgical training method comprising:
 obtaining surgical information recorded during each of a plurality of surgical performances occurring at a plurality of identified times by each of a plurality of surgeons in a surgeon network;
 determining a level of influence of each surgeon using the surgical information and the identified times;
 identifying a surgeon with a level of influence which meets a predetermined condition as a candidate for receiving training;
 training the identified surgeon operating a master console on a new surgery;
 monitoring the identified surgeon using the master console during training on the new surgery;
 supplying signals output from the master console in response to manipulation by the identified surgeon during training to control a surgical arm including a surgical device, wherein the surgical arm is in communication with the master console; and
 supplying signals from the surgical arm to the master console to provide haptic feedback to the identified surgeon during training.

17. A non-transitory storage medium storing a program for controlling a computer to perform a method according to claim 16.

18. The surgical training method according to claim 16, further comprising:
 controlling an autonomous imaging arm including an image sensor so that an image output by the image sensor is not occluded by the surgical arm during training.

19. The surgical training method according to claim 18, further comprising:
 determining if the autonomous imaging arm is subject to resistance; and
 in response to the autonomous imaging arm being subject to resistance, controlling the autonomous imaging arm so that an image output by the image sensor is from a view allowing free movement of the autonomous imaging arm.

* * * * *